(12) United States Patent
Persons et al.

(10) Patent No.: US 7,446,115 B2
(45) Date of Patent: Nov. 4, 2008

(54) PEPTIDOMIMETIC LIGANDS FOR CELLULAR RECEPTORS AND ION CHANNELS

(75) Inventors: Paul E. Persons, Westborough, MA (US); Joanne M. Holland, Brookline, MA (US); James R. Hauske, Concord, MA (US)

(73) Assignee: Sepracor, Inc., Marlborough, MA (US)

( * ) Notice: Subject to any disclaimer, the term of this patent is extended or adjusted under 35 U.S.C. 154(b) by 76 days.

(21) Appl. No.: 11/512,056

(22) Filed: Aug. 29, 2006

(65) Prior Publication Data

US 2007/0093522 A1    Apr. 26, 2007

Related U.S. Application Data

(63) Continuation of application No. 10/203,279, filed as application No. PCT/US01/06173 on Feb. 27, 2001, now Pat. No. 7,115,664.

(60) Provisional application No. 60/190,133, filed on Mar. 16, 2000.

(51) Int. Cl.
| | |
|---|---|
| *A61K 31/40* | (2006.01) |
| *A61K 31/4025* | (2006.01) |
| *A61K 31/472* | (2006.01) |
| *C07D 207/14* | (2006.01) |
| *C07D 211/56* | (2006.01) |
| *C07D 217/12* | (2006.01) |
| *C07D 223/16* | (2006.01) |

(52) U.S. Cl. ............... 514/307; 514/426; 514/317; 548/557; 546/139; 546/125; 546/244; 540/593

(58) Field of Classification Search .............. None
See application file for complete search history.

(56) References Cited

U.S. PATENT DOCUMENTS

| | | | |
|---|---|---|---|
| 4,829,053 A | 5/1989 | Raddatz et al. |
| 5,200,408 A | 4/1993 | Bru-Magniez et al. |
| 5,284,828 A | 2/1994 | Hemmi et al. |
| 5,496,928 A | 3/1996 | Ishikawa et al. |
| 5,538,950 A | 7/1996 | Hemmi et al. |
| 5,552,404 A | 9/1996 | Chang et al. |
| 5,574,159 A | 11/1996 | Chang et al. |
| 5,646,151 A | 7/1997 | Kruse et al. |
| 5,646,604 A | 7/1997 | Maruyama et al. |
| 5,658,908 A | 8/1997 | Chang et al. |
| 5,681,830 A | 10/1997 | Chang et al. |
| 5,688,955 A | 11/1997 | Kruse et al. |
| 5,744,458 A | 4/1998 | Kruse et al. |
| 5,750,646 A | 5/1998 | Coy et al. |
| 5,760,023 A | 6/1998 | Farrar et al. |
| 5,763,445 A | 6/1998 | Kruse et al. |

FOREIGN PATENT DOCUMENTS

| | | |
|---|---|---|
| EP | 0555537 A2 | 8/1993 |
| EP | 0555537 B1 | 11/2000 |
| WO | WO-93/15062 | 8/1993 |
| WO | WO-95/22557 | 8/1995 |
| WO | WO-96/40208 | 12/1996 |
| WO | WO-97/09973 | 3/1997 |
| WO | WO-97/32857 | 9/1997 |
| WO | WO-97/46240 | 12/1997 |
| WO | WO-98/42732 | 10/1998 |
| WO | WO-98/49141 | 11/1998 |
| WO | WO-99/65932 | 12/1999 |
| WO | WO-99/67206 | 12/1999 |
| WO | WO 01/10439 A1 | 2/2001 |

OTHER PUBLICATIONS

Foley, M.A., et al., "Rapid Synthesis of Novel Dipeptide Inhibitors of Human Collagenase and Gelatinase Using Solid Phase Chemistry", Bioorganic & Medicinal Chemistry Letters, vol. 6, No. 16, pp. 1905-1910, 1996.*

Foley et al.; "Rapid synthesis of noval dipeptide inhibitors of human collagenase and gelatinase using solid phase chemistry"; Bioorganic & Medicinal Chemsitry Letters, vol. 6, No. 16, pp. 1905-1910 (1996).

Ishikawa et al. (1994): STN International. HCAPLUS database, Columbus, OH. Accession No. 1994:681323 HCAPULS.

Hackler et al.; "Isolation of Relatively Large Amounts of Endomorphin-1 and Endomorphib-2 From Human Brain Cortex", Peptides, 18(10): pp. 1635-1639; (1997).

(Continued)

*Primary Examiner*—Rebecca L Anderson
*Assistant Examiner*—Michael P Barker
(74) *Attorney, Agent, or Firm*—Peter F. Corless; Edwards Angell Palmer & Dodge LLP

(57) ABSTRACT

One aspect of the present invention relates to novel peptidomometic compounds. A second aspect of the present invention relates to the use of the novel peptidomimetic compounds as ligands—agonists or antagonists—for various cellular receptors, e.g., G-protein-coupled receptors and opioid receptors, and various cellular ion channels, e.g., sodium and calcium. In certain embodiments, compounds of the present invention preferentially or selectively inhibit sodium or calcium ion channels. In certain embodiments, compounds of the present invention preferentially or selectively agonize or antagonize μ opioid receptors. In certain embodiments, compounds of the present invention preferentially or selectively inhibit sodium or calcium ion channels and agonize or antagonize μ-opioid receptors.

5 Claims, 14 Drawing Sheets

OTHER PUBLICATIONS

Martin-Schild et al.; "Localization of Endomorphin-2-Like Immunoreactivity in the Rat Medulla and Spinal Cor", Peptides, 18(10): pp. 1641-1649; (1997).

Okuda-Ashitaka et al.; "Nocistatin, a Peptide that Blocks Nociceptin Action in Pain Transmission", Nature, 392: pp. 286-289; (Mar. 19, 1989).

Sakagushi et al.; "Receptors interactions of Synthetic Morphicetin Analogs Containing Phenylalanine Homologs in Position 4", Bull. Chem. Soc. Jpn, 65(4): pp. 1052-1056; (1992).

Simon et al.; "Peptides: A Modular Approach to Drug Discovery", Proc. Natl. Acad. Sci. USA 89: pp. 9367-9371; (Oct. 1992).

Zadina et al.; "A Potent and Selective Endogenous Agonist for the μ-Opiate Receptor", Nature 386: pp. 499-502 (Apr. 3, 1997).

Zuckermann et al.; "Discovery of Nanomolar Ligands for 7-Transmembrane G-Protein-Coupled Receptors from a Diverse N-(Substituted) Glycine Peptoid Library", J. Med. Chem. 37: pp. 2678-2685; (1994).

Chemical Abstracts, vol. 125(25), abstract No. 317636, (Dec. 16 1996), B. Hartrodt et al.; "Synsthesis of New beta- Casomorphin analogs; Binding Profiled Towards Mu and Delta Opioid Receptors" XP002117511; Columbus Ohio.

Chemical Abstracts vol. 115(110, abstract No. 105427, (Sep. 16, 1991), Y. Shimohigashi et al.; "Pioid Activities of Morphiceptin-like Peptides Latent in Various Natural Proteins", XP002117512, Columbus, Ohio.

Database Chemicats [online] ComGenex Product List, Retrieved from STN, Database Accession No. 2001:789895, CAS RN: 332075-69-1, XP002173022, (Sep. 16, 1999).

Database Chemicats [online] ComGenex Product List, Retrieved from STN, Database Accession No. 2001:789894, CAS RN: 332075-68-0, XP002173023, (Sep. 16, 1999).

Database Chemicats [online] ComGenex Product List, Retrieved from STN, Database Accession No. 2001:789893, CAS RN:332075-67-9, XP002173024, (Sep. 16, 1999).

Database Chemicats [online] ComGenex Product List, Retrieved from STN, Database Accession No. 2001:789892, CAS RN: 332075-66-8, XP002173025, (Sep. 16, 1999).

Database Chemicats [online] ComGenex Product List, Retrieved from STN, Database Accession No. 2001:789891, CAS RN: 332075-65-7, XP002173026, (Sep. 16, 1999).

Database Chemicats [online] ComGenex Product List, Retrieved from STN, Database Accession No. 2001:789890, CAS RN: 332075-64-6, XP002173027, (Sep. 16, 1999).

Database Chemicats [online] ComGenex Product List, Retrieved from STN, Database Accession No. 2001: 789889, CAS RN: 332075-63-5, XP002173028, (Sep. 16, 1999).

Database Chemicats [online] ComGenex Product List, Retrieved from STN, Database Accession No. 2001: 789888, CAS RN: 332075-62-4, XP002173029, (Sep. 16, 1999).

Database Chemicats [online] ComGenex Product List, Retrieved from STN, Database Accession No. 2001: 789887, CAS RN: 332075-61-3, XP002173030, (Sep. 16, 1999).

Database Chemicats [online] ComGenex Product List, Retrieved from STN, Database Accession No. 2001: 789886, CAS RN: 332075-60-2, XP002173031, (Sep. 16, 1999).

Database Chemicats [online] ComGenex Product List, Retrieved from STN, Database Accession No. 2001: 789885, CAS RN: 332075-59-9, XP002173032, (Sep. 16, 1999).

Database Chemicats [online] ComGenex Product List, Retrieved from STN, Database Accession No. 2001: 789884, CAS RN: 332028-95-2, XP002173033, (Sep. 16, 1999).

Database Chemicats [online] ComGenex Product List, Retrieved from STN, Database Accession No.

Database Chemicats [online] ComGenex Product List, Retrieved from STN, Database Accession No. 2001:789882, CAS RN: 332028-93-0, XP002173035, (Sep. 16, 1999).

Database Chemicats [online] ComGenex Product List, Retrieved from STN, Database Accession No. 2001:789881, CAS RN: 33208-92-9, XP002173036, (Sep. 16, 1999).

Database Chemicats [online] ComGenex Product List, Retrieved from STN, Database Accession No. 2001:31780, CAS RN: 292838-84-7, XP002173037, (Sep. 16, 1999).

Database Chemicats [online] ComGenex Product List, Retrieved from STN, Database Accession No. 2001: 31779, CAS RN: 292838-83-6, XP002173038, (Sep. 16, 1999).

Database Chemicats [online] ComGenex Product List, Retrieved from STN, Database Accession No. 2001: 31778, CAS RN: 292838-82-5, XP002173039, (Sep. 16, 1999).

Database Chemicats [online] ComGenex Product List, Retrieved from STN, Database Accession No. 2001: 31777, CAS RN: 292838-81-4, XP002173040, (Sep. 16, 1999).

Database Chemicats [online] ComGenex Product List, Retrieved from STN, Database Accession No. 2001: 31776, CAS RN: 292838-80-3, XP002173041, (Sep. 16, 1999).

Database Chemicats [online] ComGenex Product List, Retrieved from STN, Database Accession No. 2001: 31775, CAS RN: 292838-79-0, XP002173042, (Sep. 16, 1999).

Database Chemicats [online] ComGenex Product List, Retrieved from STN, Database Accession No. 2001: 31774, CAS RN: 292838-78-9, XP002173043, (Sep. 16, 1999).

Database Chemicats [online] ComGenex Product List, Retrieved from STN, Database Accession No. 2001: 31773, CAS RN: 292838-77-8, XP002173044, (Sep. 16, 1999).

Database Chemicats [online] ComGenex Product List, Retrieved from STN, Database Accession No. 2001: 860620, CAS RN: 293317-75-6, XP002173045, (Sep. 16, 1999).

Database Chemicats [online] ComGenex Product List, Retrieved from STN, Database Accession No. 2001: 860619, CAS RN: 293317-75-5, XP002173046, (Sep. 16, 1999).

Database Chemicats [online] ComGenex Product List, Retrieved from STN, Database Accession No. 2001: 860618, CAS RN: 293317-73-4, XP002173047, (Sep. 16, 1999).

Database Chemicats [online] ComGenex Product List, Retrieved from STN, Database Accession No. 2001: 860617, CAS RN: 293317-72-3, XP002173048, (Sep. 16, 1999).

Database Chemicats [online] ComGenex Product List, Retrieved from STN, Database Accession No. 2001: 860616, CAS RN: 293317-71-2, XP002173049, (Sep. 16, 1999).

Database Chemicats [online] ComGenex Product List, Retrieved from STN, Database Accession No. 2001: 859547, CAS RN: 292627-74-8, XP002173050, (Sep. 16, 1999).

Database Chemicats [online] ComGenex Product List, Retrieved from STN, Database Accession No. 2001: 859546, CAS RN: 292627-73-7, XP002173051, (Sep. 16, 1999).

Database Chemicats [online] ComGenex Product List, Retrieved from STN, Database Accession No. 2001: 856648, CAS RN: 292031-73-3, XP002173052, (Sep. 16, 1999).

Database Chemicats [online] ComGenex Product List, Retrieved from STN, Database Accession No. 2001: 856590, CAS RN: 292028-84-3, XP002173053, (Sep. 16, 1999).

Database Chemicats [online] ComGenex Product List, Retrieved from STN, Database Accession No. 2001: 856589, CAS RN: 292028-79-6, XP002173054, (Sep. 16, 1999).

Database Chemicats [online] ComGenex Product List, Retrieved from STN, Database Accession No. 2001: 8566588, CAS RN: 292028-74-1, XP002173055, (Sep. 16, 1999).

* cited by examiner

PEPTIDOMIMETIC LIGANDS FOR CELLULAR RECEPTORS AND ION CHANNELS

RELATED APPLICATIONS

This application is a continuation of U.S. patent application Ser. No. 10/203,279, filed Mar. 4, 2003 now U.S. Pat. No. 7,115,664; which claims the benefit of priority to Patent Cooperation Treaty Application serial number PCT/US01/06173, filed Feb. 27, 2001; which claims the benefit of priority to U.S. Provisional Patent Application Ser. No. 60/190,133, filed Mar. 16, 2000.

BACKGROUND OF THE INVENTION

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause and signals tissue damage. In addition, acute pain syndromes can be episodic, for example recurrent discomfort from arthritis. Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment.

Millions of people suffer from chronic or intractable pain. Persistent pain varies in etiology and presentation. In some cases, symptoms and signs may be evident within a few weeks to a few months after the occurrence of an injury or the onset of disease, e.g., cancer or AIDS. Like many illnesses that at one time were not well understood, pain and its many manifestations may be poorly treated and seriously underestimated. Inappropriately treated pain seriously compromises the patient's quality of life, causing emotional suffering and increasing the risk of lost livelihood and disrupted social integration. Severe chronic pain affects both the pediatric and adult population, and often leads to mood disorders, including depression and, in rare cases, suicide.

In the last several years, health policy-makers, health professionals, regulators, and the public have become increasingly interested in the provision of better pain therapies. This interest is evidenced, in part, by the U.S. Department of Health and Human Services' dissemination of Clinical Practice Guidelines for the management of acute pain and cancer pain. There is currently no nationally accepted consensus for the treatment of chronic pain not due to cancer, yet the economic and social costs of chronic pain are substantial, with estimates ranging in the tens of billions of dollars annually.

Different classes of drugs are currently available for pain management, nonsteriodal anti-inflammatories, opioids, and adjuvant analgesics. The nonsteriodal anti-inflammatories class includes drugs such as aspirin, ibuprofen, diclofenac, acetaminophen, celecoxib, and rofecoxib. The opioid class includes morphine, oxycodone, fentanyl, and pentazocine. Adjuvant analgesics include various antidepressants, anticonvulsants, neuroleptics, corticosteroids and ion channel-blocking agents, such as carbamazepine ($Na^+$) and ziconotide ($Ca^{+2}$).

Sodium channel-blocking agents have been reported to be effective in the treatment of pain and various disease states. Anger et al. J. Med. Chem. 44(2), 115-137 (2001). They are particularly useful as local anesthetics, and in the treatment of cardiac arrhythmia. Sodium channel blockers have also been used as anticonvulsants and as neuroprotective agents for treating stroke and other brain injuries. Recently, sodium channel blockers have also proven useful in the treatment of tinnitus, commonly known as ringing of the ear (Murai et al. American Journal of Otology, 13(5), 454-464 (1992)). It has also been reported for many years that sodium channel-blocking agents may be useful in the treatment of pain, including neuropathic pain; see, for example, Tanelian et al., Pain Forum., 4(2), 75-80, (1995). There is evidence that sodium channel-blocking agents selectively suppress ectopic neural firing in injured nerves, and it is by this mechanism that they are believed to be useful for relieving pain. Studies carried out on well known sodium channel-blocking agents, for example carbamazepine, phenytpin, lidocaine, mexiletine, and the like, have shown them to be useful against various types of neuropathic pain conditions.

However, pain relief has often been obtained concomitantly with numerous adverse events and/or limitations in efficacy which have restricted tolerability of these drugs. This difficulty may be due to the disparate activities outlined above, which in turn may arise, in part, because many of the above compounds block more than one type of ion channel. For example, lidocaine and bupivacaine bind potassium channels, and it is believed that this activity is responsible for their cardiotoxic effects. A selective sodium channel blocking agent may provide increased specificity of action, reducing unwanted side effects, and permitting more freedom to vary dosage for treating the primary disorder without inducing seizures or cardiac malfunction.

Calcium channel-blocking agents have also been shown to reduce pain behaviors, mechanical hyperalgesia and allodynia. Selective voltage sensitive calcium channel blockes have been shown to be effective analgesics. Recently, ziconotide, has been reported to be effective in treating severe neuropathic pain [Hu et al. Bioorganic & Medicinal Chemistry Letters 9: 2151-2156 (1999)]. Also, co-administration of ziconotide and morphine, an opioid agonist, produced an additive or synergistic analgesic effect, see Wang et al. Pain 84: 271-281 (2000).

Opioids are the major class of analgesics used in the management of moderate to severe pain because of their effectiveness, ease of titration, and favorable risk-to-benefit ratio. Opioids produce analgesia by binding to specific receptors both within and outside the CNS. Opioid analgesics are classified as full agonists, partial agonists, or mixed agonist-antagonists, depending on the receptors to which they bind and their intrinsic activities at each receptor.

Three subclasses of opioid receptor have been identified in humans, namely the $\delta$-, $\kappa$-, and $\mu$-opioid receptors. Analgesia is thought to involve activation of $\mu$ and/or $\kappa$ receptors. Notwithstanding their low selectivity for $\mu$ over $\kappa$ receptors, it is likely that morphine and morphine-like opioid agonists produce analgesia primarily through interaction with $\mu$ receptors; selective agonists of $\kappa$ receptors in humans produce analgesia, because rather than the euphoria associated with morphine and congeners, these compounds often produce dysphoria and psychotomimetic effects. The consequences of activating $\delta$ receptors in humans remain unclear.

Although opioids can be very effective in pain management, they do cause several side effects, such as respiratory depression, constipation, physical dependence, tolerance, withdraw. These unwanted effects can severely limit their use.

The known ion channel-blocking agents and opioids have been very effective in pain management. However, they have restricted use because of several potentially severe side effects. Therefore, there is a current need for pharmaceutical agents that retain the analgesic properties of the known ion channel-blocking agents and opioids, but that have reduced side effect profiles. A single agent that has both ion channel-blocking ability and opioid binding ability may be particularly useful in pain management because of an additive or synergistic analgesic effect from a duel biochemical mechanism of action. This additive or synergistic analgesic effect would result in lower drug concentrations required for pain relief and therefore reduced side effect profiles.

SUMMARY OF THE INVENTION

One aspect of the present invention relates to novel peptidomometic compounds. A second aspect of the present invention relates to the use of the novel peptidomimetic compounds as ligands—agonists or antagonists—for various cellular receptors, e.g., G-protein-coupled receptors and opioid receptors, and various cellular ion channels, e.g., sodium and calcium. In certain embodiments, compounds of the present invention preferentially or selectively inhibit sodium or calcium ion channels. In certain embodiments, compounds of the present invention preferentially or selectively agonize or antagonize μ opioid receptors. In certain embodiments, compounds of the present invention preferentially or selectively inhibit sodium or calcium ion channels and agonize or antagonize μ-opioid receptors.

BRIEF DESCRIPTION OF THE FIGURES

FIG. 1 depicts certain compounds of the present invention made according to the combinatorial methods described in Example 30.

FIG. 2 depicts certain compounds of the present invention made according to the combinatorial methods described in Example 30.

FIG. 3 depicts certain compounds of the present invention made according to the combinatorial methods described in Example 30.

FIG. 4 depicts certain compounds of the present invention made according to the combinatorial methods described in Example 30.

FIG. 5 depicts certain compounds of the present invention made according to the combinatorial methods described in Example 30.

FIG. 6 depicts certain compounds of the present invention made according to the combinatorial methods described in Example 30.

FIG. 7 depicts certain compounds of the present invention made according to the combinatorial methods described in Example 30.

FIG. 8 depicts certain compounds of the present invention made according to the combinatorial methods described in Example 30.

FIG. 9 depicts certain compounds of the present invention made according to the combinatorial methods described in Example 30.

FIG. 10 depicts certain compounds of the present invention made according to the combinatorial methods described in Example 30.

FIG. 11 depicts certain compounds of the present invention made according to the combinatorial methods described in Example 30.

FIG. 12 depicts certain compounds of the present invention made according to the combinatorial methods described in Example 30.

FIG. 13 depicts certain compounds of the present invention made according to the combinatorial methods described in Example 30.

FIG. 14 depicts certain compounds of the present invention made according to the combinatorial methods described in Example 30.

FIGS. 15 through 198 depict certain compounds.

DETAILED DESCRIPTION OF THE INVENTION

Figure 31:
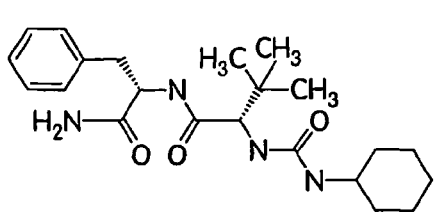
Figure 32:
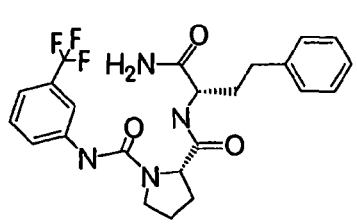
Figure 33:
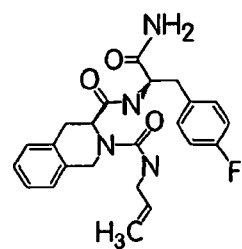
Figure 34:
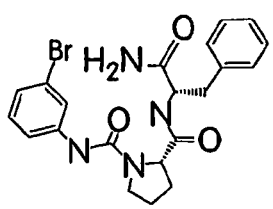
Figure 35:
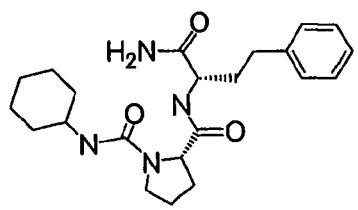
Figure 36:
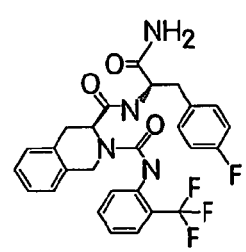
Figure 37:
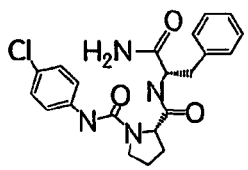
Figure 38:
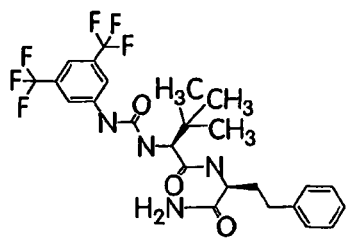
Figure 39:
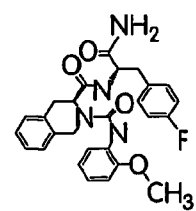
Figure 40:
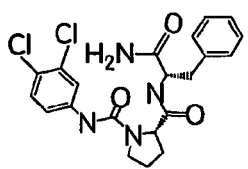
Figure 41:
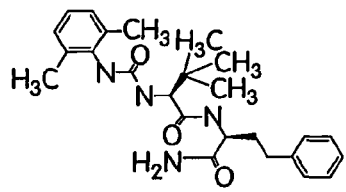
Figure 42:
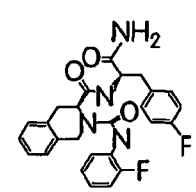
Figure 43:
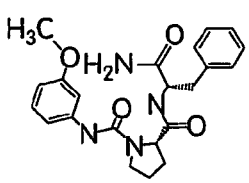
Figure 44:
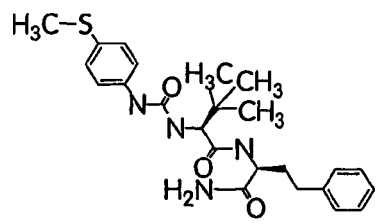
Figure 45:
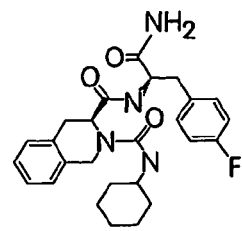
Figure 61:
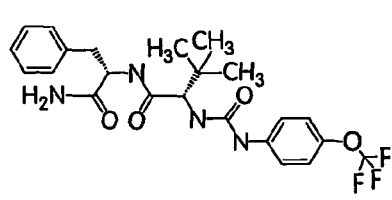
Figure 62:
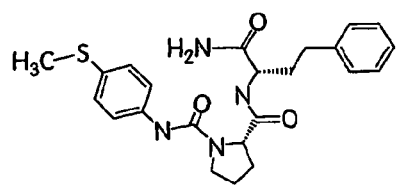
Figure 63:
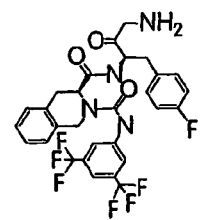
Figure 64:
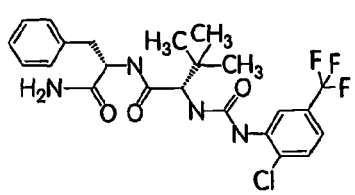
Figure 65:
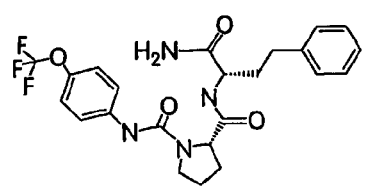
Figure 66:
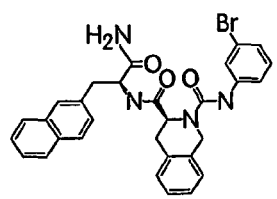
Figure 67:
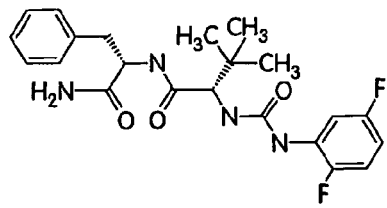
Figure 68:
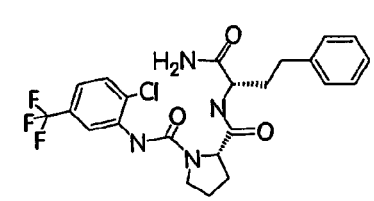
Figure 69:
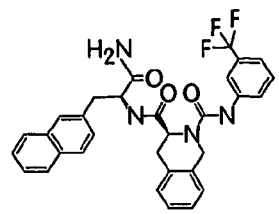
Figure 70:
Figure 71:
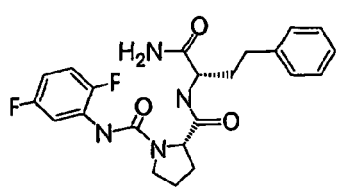
Figure 72:
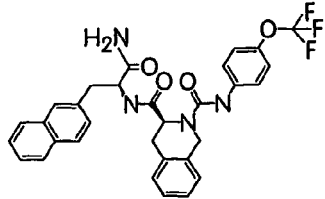
Figure 73:
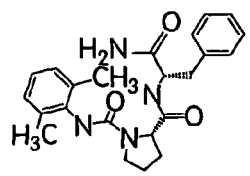
Figure 74:
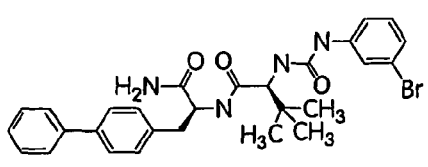
Figure 75:
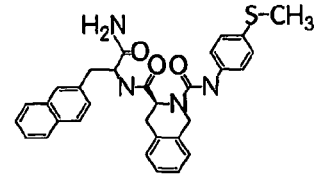
Figure 91:
Figure 92:
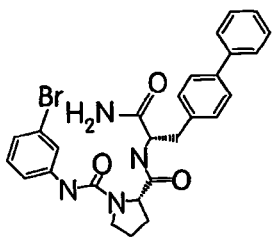
Figure 93:
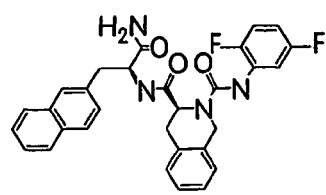
Figure 94:
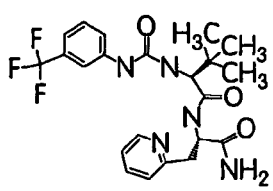
Figure 95:
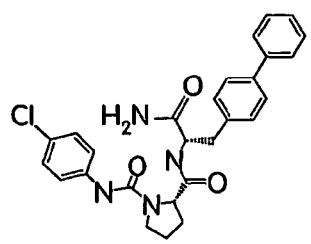
Figure 96:
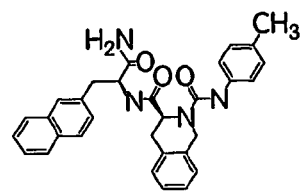
Figure 97:
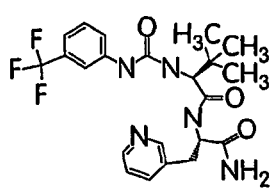
Figure 98:
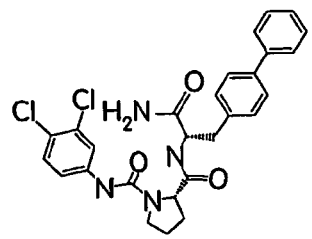
Figure 99:
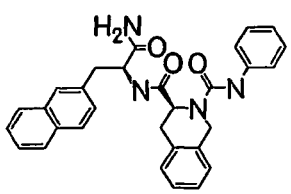
Figure 100:
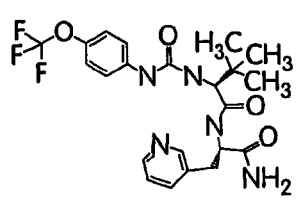
Figure 101:
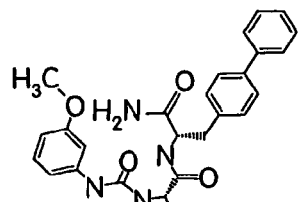
Figure 102:
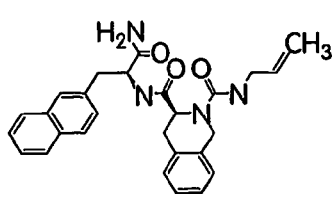
Figure 103:
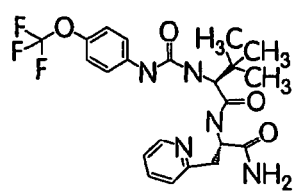
Figure 104:
Figure 105:
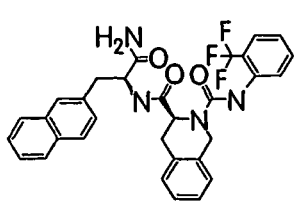
Figure 136:
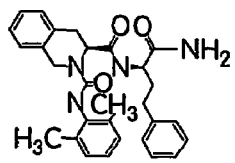
Figure 137:
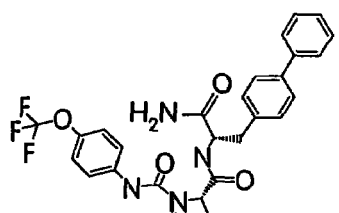
Figure 138:
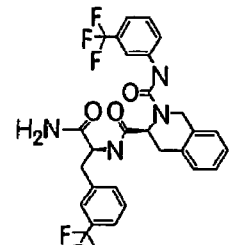
Figure 139:
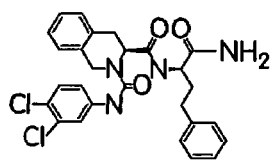
Figure 140:
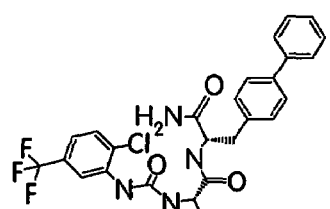
Figure 141:
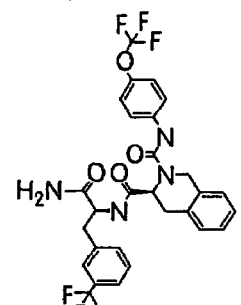
Figure 142:
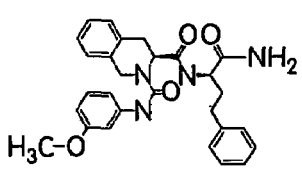
Figure 143:
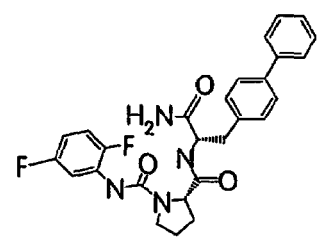
Figure 144:
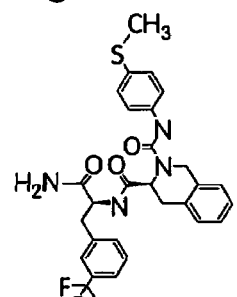
Figure 145:
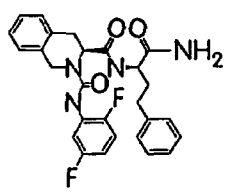
Figure 146:
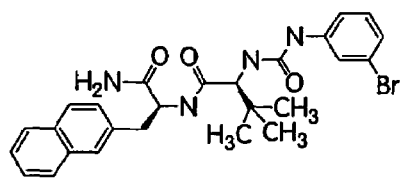
Figure 147:
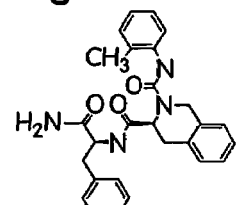
Figure 148:
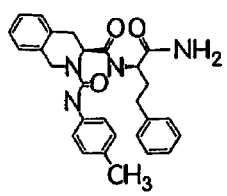
Figure 149:
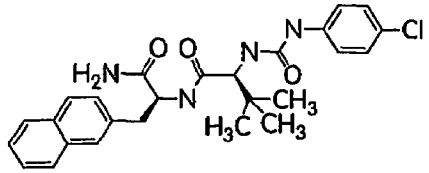
Figure 150:
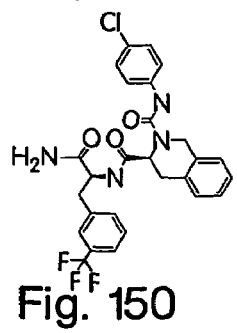
Figure 151:
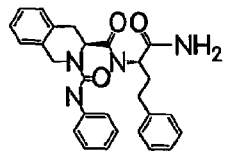
Figure 152:
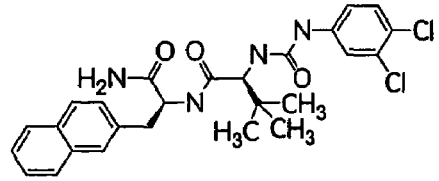
Figure 153:
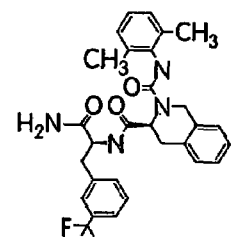
Figure 154:
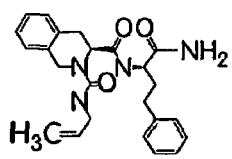
Figure 155:
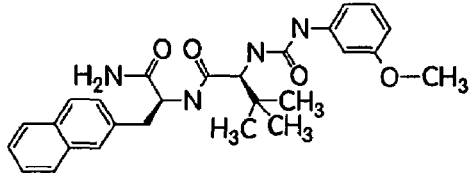
Figure 156:
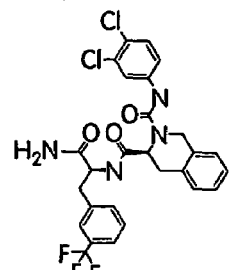
Figure 157:
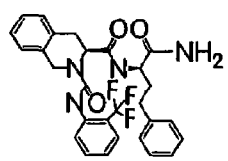
Figure 158:
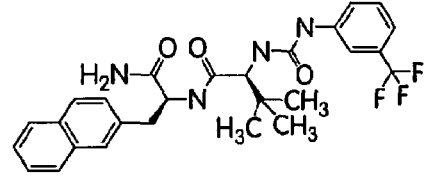
Figure 159:
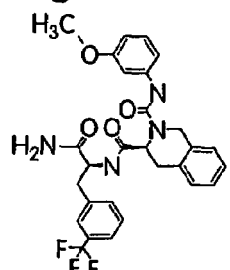
Figure 160:
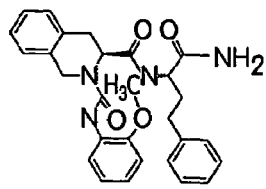
Figure 161:
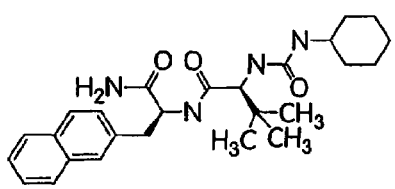
Figure 162:
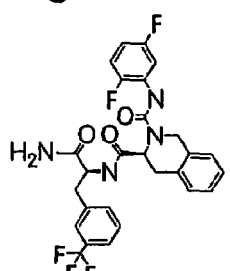
Figure 163:
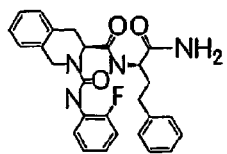
Figure 164:
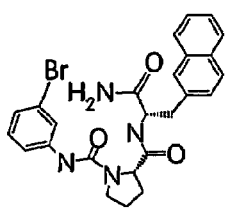
Figure 165:
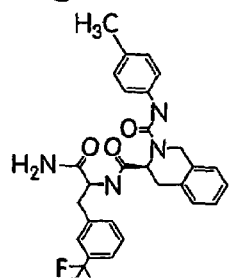
Figure 166:
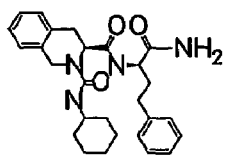
Figure 167:
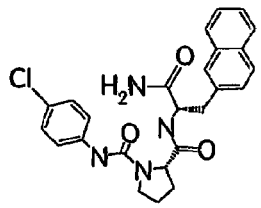
Figure 168:
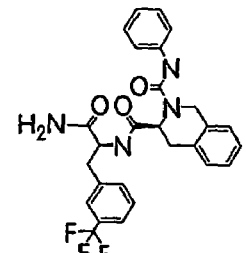
Figure 169:
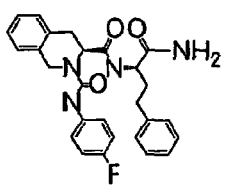
Figure 170:
Figure 171:
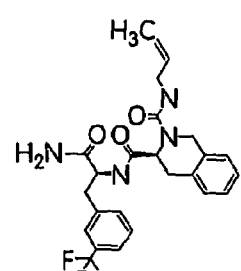
Figure 172:
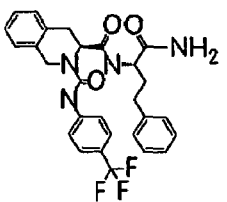
Figure 173:
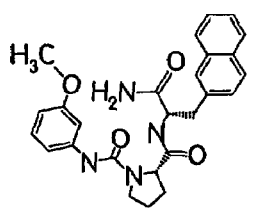
Figure 174:
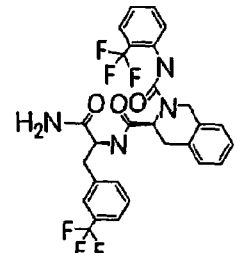
Figure 175:
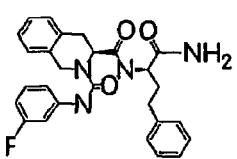
Figure 176:
Figure 177:
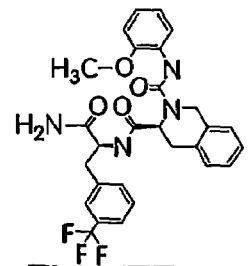
Figure 178:
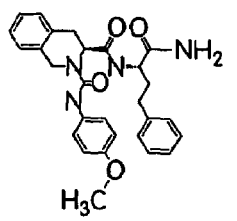
Figure 179:
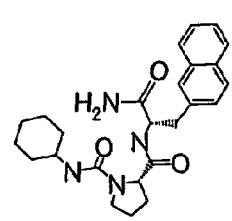
Figure 180:
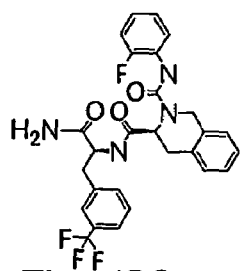
Figure 181:
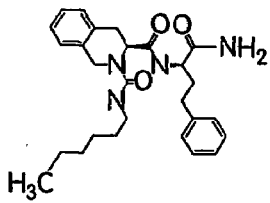
Figure 182:
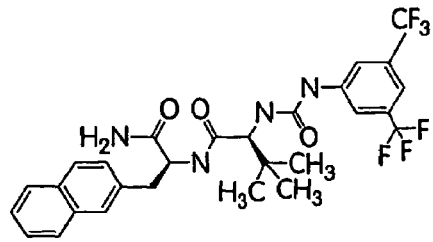
Figure 183:
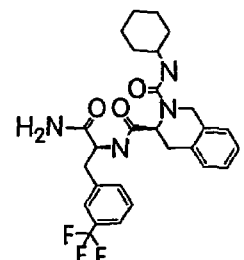
Figure 184:
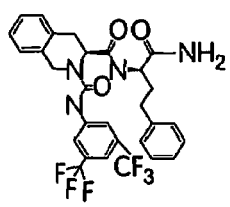
Figure 185:
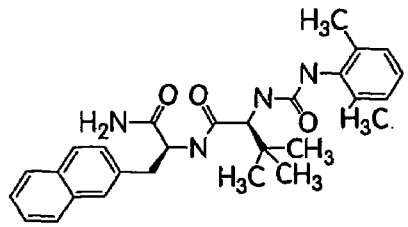
Figure 186:
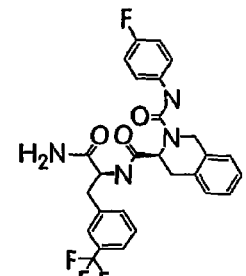
Figure 187:
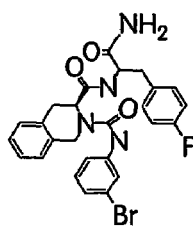
Figure 188:
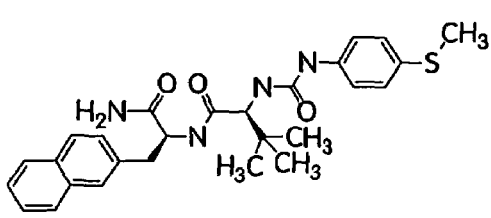
Figure 189:
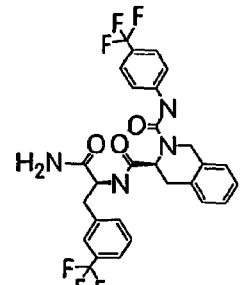
Figure 190:
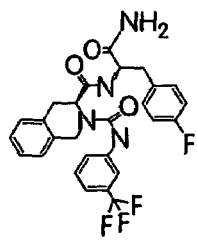
Figure 191:
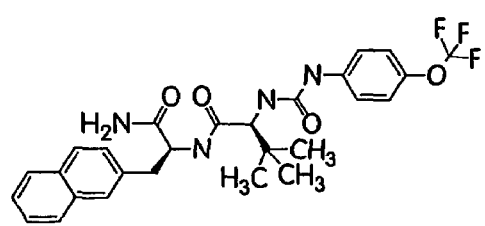
Figure 192:
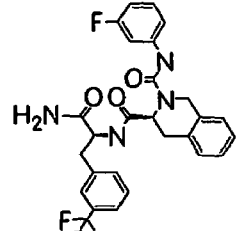
Figure 193:
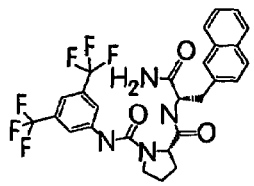
Figure 194:
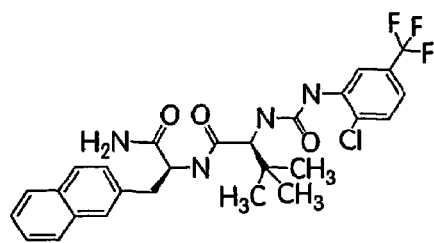
Figure 195:
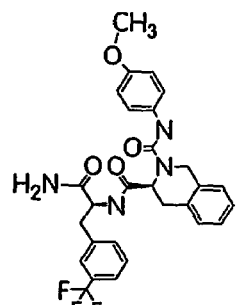
Figure 196:
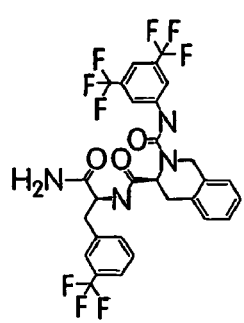
Figure 197:
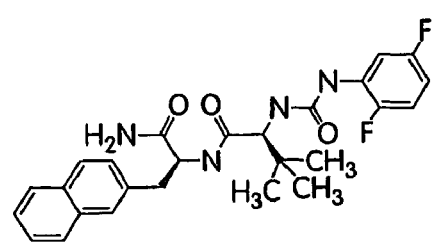
Figure 198:
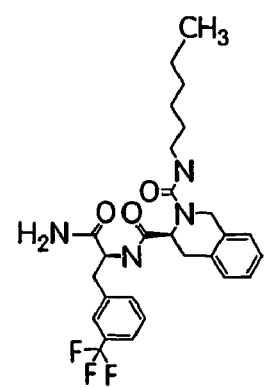

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause (e.g., hip fracture) and signals tissue damage. The associated effect is often anxiety, and the concomitant physiologic findings are those of sympathetic stimulation (e.g., tachycardia, tachypnea, diaphoresis). In addition, acute pain syndromes can be episodic, for example recurrent discomfort from arthritis.

Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment. Chronic pain can be divided broadly into that which is inferred to be predominantly somatogenic and that which is inferred to be predominantly psychogenic. A similar classification based on inferred pathophysiology designates chronic pain as nociceptive (commensurate with ongoing activation of pain-sensitive nerve fibers), neuropathic (due to aberrant somatosensory processing in afferent neural pathways), or psychogenic.

Nociceptive pain can be somatic or visceral. Most chronic pain in the elderly is nociceptive and somatic; arthritis, cancer pain, and myofascial pain are most common. Relief is likely with removal of the peripheral cause (e.g., reducing periarticular inflammation), and analgesic drugs are often effective.

A common subtype of neuropathic pain, known collectively as peripheral neuropathic pain, is presumably sustained by mechanisms that involve disturbances in the peripheral nerve or nerve root; neuroma formation after axonal injury and nerve compression are the two major processes. Another subtype of neuropathic pain is related to the reorganization of nociceptive information processing by the CNS; it persists without ongoing activation of pain-sensitive fibers. This type of pain, known collectively as the deafferentation syndromes, includes postherpetic neuralgia, central pain (which can result from a lesion at any level of the CNS), phantom limb pain, and others. A third subtype of neuropathic pain, often called sympathetically maintained pain, can be ameliorated by interruption of sympathetic nerves to the painfuil area; the prototypic disorder is reflex sympathetic dystrophy. The precise mechanisms involved in these disorders are conjectural, but all can produce an unfamiliar pain, often described as burning and stabbing. Currently, this type of pain responds poorly to analgesics.

Some patients have persistent pain without either nociceptive foci or evidence of a neuropathic mechanism for the pain. Many others have nociceptive lesions that do not sufficiently explain the degree of pain and disability. Psychopathologic processes account for these complaints in some patients. If no evidence for a psychological cause is found, the pain is referred to as idiopathic. Many patients have an idiopathic pain syndrome that is best described by the generic diagnosis chronic nonmalignant pain syndrome, a term denoting pain and disability disproportionate to an identifiable somatic cause and usually related to a more pervasive set of abnormal illness behaviors. Some of these patients may be labeled by the more formal psychiatric diagnosis of somatoform pain disorder. Others have complaints that constitute a specific pain diagnosis, most commonly the failed low back syndrome or atypical facial pain. Still others have significant organic lesions (e.g., lumbar arachnoiditis) but also have a clear psychological contribution associated with excessive disability. Diagnosis may be difficult, but the relative contributions of both organic and psychological components of the pain can be defined.

Another clinically useful classification of chronic pain is broadly syndromic. For example, chronic pain may be part of a medical illness (e.g., cancer or arthritis). A mixture of pathophysiologic mechanisms may be involved; e.g., tumor invasion of nerve and bone may cause neuropathic and somatic nociceptive pains, respectively, and psychological factors may be prominent.

Different classes of drugs are currently available for pain management, nonsteriodal anti-inflammatories, opioids, and adjuvant analgesics. The nonsteriodal anti-inflammatories class includes drugs such as aspirin, ibuprofen, diclofenac, acetaminophen, celecoxib, and rofecoxib. The opioid class includes morphine, oxycodone, fentanyl, and pentazocine. Adjuvant analgesics include various antidepressants, anticonvulsants, neuroleptics, corticosteroids and ion channel-blocking agents, such as carbamazepine ($Na^+$) and ziconotide ($Ca^{+2}$).

Opioids, specifically ligands for the μ-opioid receptor, are the major class of analgesics used in the management of moderate to severe pain because of their effectiveness, ease of titration, and favorable risk-to-benefit ratio. Unfortunately, the opioids currently available are addictive to varying degrees. Research into the development of new, selective ligands for opioid receptors holds the promise of yielding potent analgesics that lack the addictive characteristics of morphine and its congeners. Applicants herein disclose novel analgesics, including selective ligands for opioid receptors. Individual compounds described herein promise to have agonistic, antagonistic, and hybrid effects on opioid and other cellular receptors. Additionally, new compounds reported herein may possess analgesic properties free from the reward-seeking behavior and potential for physical dependence associated with morphine and heroin.

Sodium channel blockers are commonly used in the treatment of pain, tinnitus, arrhythmia, ischemic stroke, and epilepsy. Some are used in anesthesia, particularly local anesthesia Many of the sodium channel blockers currently in use block multiple ion channels, including potassium and calcium channels, and thus are associated with undesirable cardiac and CNS side effects. Some of these drugs can cause seizures, tremors, arrhytmnias, or hypotension.

Calcium channel-blocking agents have also been shown to reduce pain behaviors, mechanical hyperalgesia and allodynia. Selective voltage sensitive calcium channel blockes have been shown to be effective analgesics. Recently, ziconotide, has been reported to be effective in treating severe neuropathic pain [Hu et al. Bioorganic & Medicinal Chemistry Letters 9: 2151-2156 (1999)]. Also, co-administration of ziconotide and morphine, an opioid agonist, produced an additive or synergistic analgesic effect. See Wang et al. Pain 84: 271-281 (2000).

The known ion channel-blocking agents and opioids have been very effective in pain management. However, they have restricted use because of several potentially severe side effects. Therefore, there is a current need for pharmaceutical agents that retain the analgesic properties of the known ion channel-blocking agents and opioids, but that have reduced side effect profiles. A single agent that has both ion channel-blocking ability and opioid binding ability may be particularly useful in pain management because of an additive or synergistic analgesic effect from a duel biochemical mechanism of action. This additive or synergistic analgesic effect would result in lower drug concentrations required for pain relief and therefore reduced side effect profiles. In addition, new compounds reported herein may possess properties for the treatment of physical or psychological additions, psychiatric disorders, and neurological pathologies, such as tinnitus.

The μ-opioid receptor ion channel receptors are members of a family of cell surface proteins that permit intracellular transduction of extracellular signals. Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A. G., Ann. Rev. Biochem. 56: 615-649 (1987), Strader, C. D. et al. The FASEB Journal 3: 1825-1832 (1989), Kobilka, B. K., et al. Nature 329:75-79 (1985) and Young et al. Cell 45: 711-719 (1986)). Among the G protein-coupled receptors that have been identified and cloned are the substance K receptor, the angiotensin receptor, the alpha— and beta-adrenergic receptors and the serotonin receptors. G protein-coupled receptors share a conserved structural motif. The general and common structural features of the G protein-coupled receptors are the existence of seven hydrophobic stretches of about 20-25 amino acids each surrounded by eight hydrophilic regions of variable length. It has been postulated that each of the seven hydrophobic regions forms a transmembrane alpha helix and the intervening hydrophilic regions form alternately intracellularly and extracellularly exposed loops. The third cytosolic loop between transmembrane domains five and six is the intracellular domain responsible for the interaction with G proteins. G protein-coupled receptors are known to be inducible. This inducibility was originally described in lower eukaryotes. For example, the cAMP receptor of the cellular slime mold, Dictyostelium, is induced during differentiation (Klein et al., Science 241: 1467-1472 (1988). During the Dictyostelium discoideum differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235-239 (1989) and Devreotes, P., Science 245: 1054-1058 (1989)).

Definitions

For convenience, certain terms employed in the specification, examples, and appended claims are collected here.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

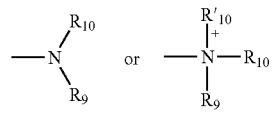

wherein $R_9$, $R_{10}$ and $R'_{10}$ each independently represent a group permitted by the rules of valence.

The term "acylamino" is art-recognized and refers to a moiety that can be represented by the general formula:

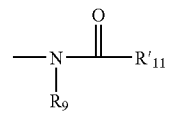

wherein $R_9$ is as defined above, and $R'_{11}$ represents a hydrogen, an alkyl an alkenyl or —(CH$_2$)$_m$—R$_8$, where m and R$_8$ are as defined above.

The term "amido" is art recognized as an amino-substituted carbonyl and includes a moiety that can be represented by the general formula:

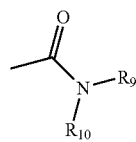

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

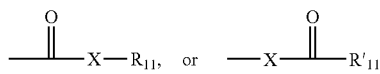

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m-R_8$, where m and $R_8$ are described above.

The term "sulfonate" is art recognized and includes a moiety that can be represented by the general formula:

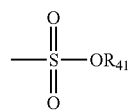

in which $R_{41}$ is an electron pair, hydrogen, alkyl cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

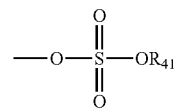

in which $R_{41}$ is as defined above.

The term "sulfonylamino" is art recognized and includes a moiety that can be represented by the general formula:

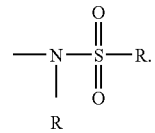

The term "sulfamoyl" is art-recognized and includes a moiety that can be represented by the general formula:

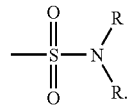

The term "sulfonyl", as used herein, refers to a moiety that can be represented by the general formula:

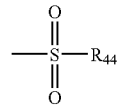

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

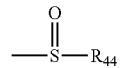

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m-R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalknyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

Compounds of the Invention.

In certain embodiments, the compounds of the present invention are represented by general structure A:

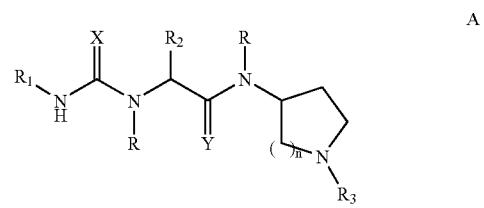

wherein
X represents O or S;
Y represents $H_2$, O or S;
R represents independently for each occurrence H, alkyl, aryl, heteroaryl, aralkyl or heteroaralkyl;
$R_1$ represents alkyl, aryl, heteroaryl, aralkyl or heteroaralkyl;
$R_2$ represents allyl, aryl, heteroaryl, aralkyl or heteroaralkyl;
$R_3$ represents H, alkyl, aryl, heteroaryl, aralkyl, heteroaralkyl or acyl;
n is 1 or 2; and
the stereochemical configuration at any stereocenter of a compound represented by A may be R, S, or a mixture of these configurations.

In certain embodiments, the compounds of the present invention are represented by general structure A and the attendant definitions, wherein X represents O.

In certain embodiments, the compounds of the present invention are represented by general structure A and the attendant definitions, wherein Y represents O or $H_2$.

In certain embodiments, the compounds of the present invention are represented by general structure A and the attendant definitions, wherein Y represents O.

In certain embodiments, the compounds of the present invention are represented by general structure A and the attendant definitions, wherein Y represents $H_2$.

In certain embodiments, the compounds of the present invention are represented by general structure A and the attendant definitions, wherein R represents independently for each occurrence H, alkyl, aralkyl or heteroaralkyl.

In certain embodiments, the compounds of the present invention are represented by general structure A and the attendant definitions, wherein $R_1$ represents aryl or heteroaryl.

In certain embodiments, the compounds of the present invention are represented by general structure A and the attendant definitions, wherein $R_2$ represents alkyl, aralkyl or heteroaralkyl.

In certain embodiments, the compounds of the present invention are represented by general structure A and the attendant definitions, wherein $R_2$ represents alkyl.

In certain embodiments, the compounds of the present invention are represented by general structure A and the attendant definitions, wherein $R_3$ represents alkyl, aralkyl or heteroaralkyl.

In certain embodiments, the compounds of the present invention are represented by general structure A and the attendant definitions, wherein $R_3$ represents aralkyl.

In certain embodiments, the compounds of the present invention are represented by general structure A and the attendant definitions, wherein X represents O; and Y represents O or $H_2$.

In certain embodiments, the compounds of the present invention are represented by general structure A and the attendant definitions, wherein X represents O; and Y represents O.

In certain embodiments, the compounds of the present invention are represented by general structure A and the attendant definitions, wherein X represents O; and Y represents $H_2$.

In certain embodiments, the compounds of the present invention are represented by general structure A and the attendant definitions, wherein X represents O; Y represents O or $H_2$; and $R_1$ represents aryl or heteroaryl.

In certain embodiments, the compounds of the present invention are represented by general structure A and the attendant definitions, wherein X represents O; Y represents O or $H_2$; and $R_2$ represents alkyl, aralkyl or heteroaralkyl.

In certain embodiments, the compounds of the present invention are represented by general structure A and the attendant definitions, wherein X represents O; Y represents O or $H_2$; and $R_2$ represents alkyl.

In certain embodiments, the compounds of the present invention are represented by general structure A and the attendant definitions, wherein X represents O; Y represents O or $H_2$; and $R_3$ represents alkyl, aralkyl or heteroaralkyl.

In certain embodiments, the compounds of the present invention are represented by general structure A and the attendant definitions, wherein X represents O; Y represents O or $H_2$; and $R_3$ represents aralkyl.

In certain embodiments, the compounds of the present invention are represented by general structure A and the attendant definitions, wherein X represents O; Y represents O or $H_2$; $R_1$ represents aryl or heteroaryl; and $R_2$ represents alkyl, aralkyl or heteroaralkyl.

In certain embodiments, the compounds of the present invention are represented by general structure A and the attendant definitions, wherein X represents O; Y represents O or $H_2$; $R_1$ represents aryl or heteroaryl; $R_2$ represents alkyl, aralkyl or heteroaralkyl; and $R_3$ represents alkyl, aralkyl or heteroaralkyl.

In certain embodiments, the compounds of the present invention are represented by general structure A and the attendant definitions, or any of the narrower definitions, wherein said compound is a single enantiomer.

In assays based on mammalian G-protein-coupled receptors, opioid receptors or ion channels, certain compounds according to general structure A have $IC_{50}$ values less than 10 µM, more preferably less than 5 µM, and most preferably less than 1 µM.

In assays based on mammalian ion channels, certain compounds according to general structure A have $IC_{50}$ values less than 10 µM against at least one type of ion channel, more preferably less than 5 µM, and most preferably less than 1 µM.

In assays based on opioid receptors from mammalian brain, certain compounds according to general structure A have $IC_{50}$ values less than 10 µM against at least one subclass of opioid receptor, more preferably less than 5 µM, and most preferably less than 1 µM.

In assays based on mammalian ion channels and based on opioid receptors from mammalian brain, certain compounds according to general structure A have $IC_{50}$ values less than 10 µM against at least one type of ion channel and against at least one subclass of opioid receptor, more preferably less than 5 µM, and most preferably less than 1 µM.

In certain embodiments, the compounds of the present invention are represented by general structure B:

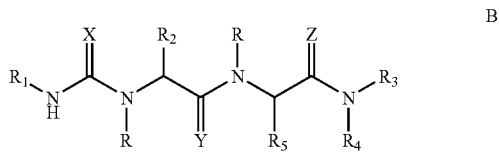

wherein
X represents O or S;
Y represents $H_2$, O or S;
Z represents $H_2$, O or S;
R represents independently for each occurrence H, alkyl, aryl, heteroaryl, aralkyl or heteroaralkyl;
$R_1$ represents alkyl, aryl, heteroaryl, aralkyl or heteroaralkyl;
$R_2$ represents independently for each occurrence alkyl, aryl, heteroaryl, aralkyl or heteroaralkyl;
$R_3$ represents H, alkyl, aryl, heteroaryl, aralkyl, heteroaralkyl or acyl;
$R_4$ represents H, alkyl, aryl, heteroaryl, aralkyl or heteroaralkyl;
$R_5$ represents independently for each occurrence H, alkyl, aryl, heteroaryl, aralkyl or heteroaralkyl;
a vicinal pair of R and $R_2$ may be connected by a covalent bond;
$R_3$ and $R_4$ may be connected by a covalent bond, or both of them may be bonded to an instance of NR, O, or S; and
the stereochemical configuration at any stereocenter of a compound represented by B may be R, S, or a mixture of these configurations.

In certain embodiments, the compounds of the present invention are represented by general structure B and the attendant definitions, wherein X represents O.

In certain embodiments, the compounds of the present invention are represented by general structure B and the attendant definitions, wherein Y represents O or $H_2$.

In certain embodiments, the compounds of the present invention are represented by general structure B and the attendant definitions, wherein Y represents O.

In certain embodiments, the compounds of the present invention are represented by general structure B and the attendant definitions, wherein Y represents $H_2$.

In certain embodiments, the compounds of the present invention are represented by general structure B and the attendant definitions, wherein R represents independently for each occurrence H, alkyl, aralkyl or heteroaralkyl.

In certain embodiments, the compounds of the present invention are represented by general structure B and the attendant definitions, wherein $R_1$ represents aryl or heteroaryl.

In certain embodiments, the compounds of the present invention are represented by general structure B and the attendant definitions, wherein $R_2$ represents alkyl, aralkyl or heteroaralkyl.

In certain embodiments, the compounds of the present invention are represented by general structure B and the attendant definitions, wherein $R_2$ represents alkyl.

In certain embodiments, the compounds of the present invention are represented by general structure B and the attendant definitions, wherein $R_3$ represents H, alkyl, aralkyl or heteroaralkyl.

In certain embodiments, the compounds of the present invention are represented by general structure B and the attendant definitions, wherein $R_3$ represents H, or alkyl.

In certain embodiments, the compounds of the present invention are represented by general structure B and the attendant definitions, wherein X represents O; and Y represents O or $H_2$.

In certain embodiments, the compounds of the present invention are represented by general structure B and the attendant definitions, wherein X represents O; and Y represents O.

In certain embodiments, the compounds of the present invention are represented by general structure B and the attendant definitions, wherein X represents O; and Y represents $H_2$.

In certain embodiments, the compounds of the present invention are represented by general structure B and the attendant definitions, wherein X represents O; Y represents O or $H_2$; and $R_1$ represents aryl or heteroaryl.

In certain embodiments, the compounds of the present invention are represented by general structure B and the attendant definitions, wherein X represents O; Y represents O or $H_2$; and $R_2$ represents alkyl, aralkyl or heteroaralkyl.

In certain embodiments, the compounds of the present invention are represented by general structure B and the attendant definitions, wherein X represents O; Y represents O or $H_2$; and $R_2$ represents alkyl.

In certain embodiments, the compounds of the present invention are represented by general structure B and the attendant definitions, wherein X represents O; Y represents O or $H_2$; and $R_3$ represents H, alkyl, aralkyl or heteroaralkyl.

In certain embodiments, the compounds of the present invention are represented by general structure B and the attendant definitions, wherein X represents O; Y represents O or $H_2$; and $R_3$ represents H, or alkyl.

In certain embodiments, the compounds of the present invention are represented by general structure B and the attendant definitions, wherein X represents O; Y represents O or $H_2$; $R_1$ represents aryl or heteroaryl; and $R_2$ represents alkyl, aralkyl or heteroaralkyl.

In certain embodiments, the compounds of the present invention are represented by general structure B and the attendant definitions, wherein X represents O; Y represents O or $H_2$; $R_1$ represents aryl or heteroaryl; $R_2$ represents alkyl, aralkyl or heteroaralkyl; and $R_3$ represents H, alkyl, aralkyl or heteroaralkyl.

In certain embodiments, the compounds of the present invention are represented by general structure B and the attendant definitions, wherein X represents O; Y represents O or $H_2$; Z represents $H_2$; R represents H; $R_1$ represents 3-(trifluoromethyl)phenyl; $R_2$ represents tert-butyl; $R_3$ represents H; $R_4$ represents H; and $R_5$ represents benzyl.

In certain embodiments, the compounds of the present invention are represented by general structure B and the attendant definitions, or any of the narrower definitions, wherein said compound is a single enantiomer.

In assays based on mammalian G-protein-coupled receptors, opioid receptors or ion channels, certain compounds according to general structure B have $IC_{50}$ values less than 10 µM, more preferably less than 5 µM, and most preferably less than 1 µm.

In assays based on mammalian ion channels, certain compounds according to general structure B have $IC_{50}$ values less than 10 µM against at least one type of ion channel, more preferably less than 5 µM, and most preferably less than 1 µM.

In assays based on opioid receptors from mammalian brain, certain compounds according to general structure B have $IC_{50}$ values less than 10 µM against at least one subclass of opioid receptor, more preferably less than 5 µM, and most preferably less than 1 µM.

In assays based on mammalian ion channels and based on opioid receptors from mammalian brain, certain compounds according to general structure B have $IC_{50}$ values less than 10 µM against at least one type of ion channel and against at least one subclass of opioid receptor, more preferably less than 5 µM, and most preferably less than 1 µM.

In certain embodiments, the compounds of the present invention are represented by general structure C:

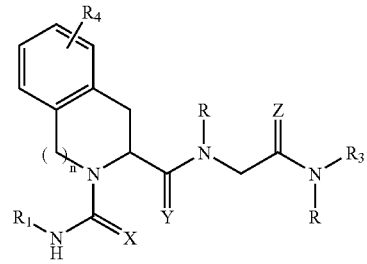

wherein
X represents O or S;
Y represents $H_2$, O or S;
Z represents $H_2$, O or S;
R represents independently for each occurrence H, alkyl, aryl, heteroaryl, aralkyl or heteroaralkyl;
$R_1$ represents alkyl, aryl, heteroaryl, aralkyl or heteroaralkyl;
$R_3$ represents H, alkyl, aryl, heteroaryl, aralkyl, heteroaralkyl or acyl;
$R_4$ is absent or present 1, 2, 3 or 4 times;
$R_4$ represents independently for each occurrence alkyl, aryl, alkenyl, alkynyl, heteroaryl, aralkyl, heteroaralkyl, halogen, —$N(R)_2$, formyl, acyl, —$CO_2R$, —$CONR_2$, —$O_2CR$, acylamino, —SR, or —OR;
n is 1 or 2; and
the stereochemical configuration at any stereocenter of a compound represented by C may be R, S, or a mixture of these configurations.

In certain embodiments, the compounds of the present invention are represented by general structure C and the attendant definitions, wherein X represents O.

In certain embodiments, the compounds of the present invention are represented by general structure C and the attendant definitions, wherein Y represents O or $H_2$.

In certain embodiments, the compounds of the present invention are represented by general structure C and the attendant definitions, wherein Y represents O.

In certain embodiments, the compounds of the present invention are represented by general structure C and the attendant definitions, wherein Y represents $H_2$.

In certain embodiments, the compounds of the present invention are represented by general structure C and the attendant definitions, wherein R represents independently for each occurrence H, alkyl, aralkyl or heteroaralkyl.

In certain embodiments, the compounds of the present invention are represented by general structure C and the attendant definitions, wherein $R_1$ represents aryl or heteroaryl.

In certain embodiments, the compounds of the present invention are represented by general structure C and the attendant definitions, wherein $R_3$ represents H, alkyl, aralkyl or heteroaralkyl.

In certain embodiments, the compounds of the present invention are represented by general structure C and the attendant definitions, wherein $R_3$ represents H, or alkyl.

In certain embodiments, the compounds of the present invention are represented by general structure C and the attendant definitions, wherein $R_4$ is absent.

In certain embodiments, the compounds of the present invention are represented by general structure C and the attendant definitions, wherein X represents O; and Y represents O or $H_2$.

In certain embodiments, the compounds of the present invention are represented by general structure C and the attendant definitions, wherein X represents O; and Y represents O.

In certain embodiments, the compounds of the present invention are represented by general structure C and the attendant definitions, wherein X represents O; and Y represents $H_2$.

In certain embodiments, the compounds of the present invention are represented by general structure C and the attendant definitions, wherein X represents O; Y represents O or $H_2$; and $R_1$ represents aryl or heteroaryl.

In certain embodiments, the compounds of the present invention are represented by general structure C and the attendant definitions, wherein X represents O; Y represents O or $H_2$; and $R_3$ represents H, alkyl, aralkyl or heteroaralkyl.

In certain embodiments, the compounds of the present invention are represented by general structure C and the attendant definitions, wherein X represents O; Y represents O or $H_2$; and $R_3$ represents H, or alkyl.

In certain embodiments, the compounds of the present invention are represented by general structure C and the attendant definitions, wherein X represents O; Y represents O or $H_2$; and $R_4$ is absent.

In certain embodiments, the compounds of the present invention are represented by general structure C and the attendant definitions, wherein X represents O; Y represents O or $H_2$; $R_1$ represents aryl or heteroaryl; and $R_3$ represents H, alkyl, aralkyl or heteroaralkyl.

In certain embodiments, the compounds of the present invention are represented by general structure C and the attendant definitions, wherein X represents O; Y represents O or $H_2$; $R_1$ represents aryl or heteroaryl; $R_3$ represents H, alkyl, aralkyl or heteroaralkyl; and $R_4$ is absent.

In certain embodiments, the compounds of the present invention are represented by general structure C and the attendant definitions, or any of the narrower definitions, wherein said compound is a single enantiomer.

In assays based on mammalian G-protein-coupled receptors, opioid receptors or ion channels, certain compounds according to general structure C have $IC_{50}$ values less than 10 µM, more preferably less than 5 µM, and most preferably less than 1 µM.

In assays based on mammalian ion channels, certain compounds according to general structure C have $IC_{50}$ values less than 10 µM against at least one type of ion channel, more preferably less than 5 µM, and most preferably less than 1 µM.

In assays based on opioid receptors from mammalian brain, certain compounds according to general structure C have $IC_{50}$ values less than 10 µM against at least one subclass of opioid receptor, more preferably less than 5 µM, and most preferably less than 1 µM.

In assays based on mammalian ion channels and based on opioid receptors from mammalian brain, certain compounds according to general structure C have $IC_{50}$ values less than 10 µM against at least one type of ion channel and against at least one subclass of opioid receptor, more preferably less than 5 µM, and most preferably less than 1 µM.

In certain embodiments, the compounds of the present invention are represented by general structure D:

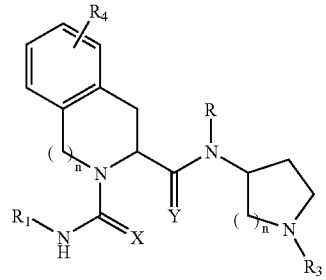

wherein
X represents O or S;
Y represents $H_2$, O or S;
R represents independently for each occurrence H, alkyl, aryl, heteroaryl, aralkyl or heteroaralkyl;
$R_1$ represents alkyl, aryl, heteroaryl, aralkyl or heteroaralkyl;
$R_3$ represents H, alkyl, aryl, heteroaryl, aralkyl, heteroaralkyl or acyl;
$R_4$ is absent or present 1, 2, 3 or 4 times;
$R_4$ represents independently for each occurrence alkyl, aryl, alkenyl, alkynyl, heteroaryl, aralkyl, heteroaralkyl, halogen, —N(R)$_2$, formyl, acyl, —CO$_2$R, —CONR$_2$, —O$_2$CR, acylamino, —SR, or —OR;
n is independently for each occurrence 1 or 2; and
the stereochemical configuration at any stereocenter of a compound represented by D may be R, S, or a mixture of these configurations.

In certain embodiments, the compounds of the present invention are represented by general structure D and the attendant definitions, wherein X represents O.

In certain embodiments, the compounds of the present invention are represented by general structure D and the attendant definitions, wherein Y represents O or $H_2$.

In certain embodiments, the compounds of the present invention are represented by general structure D and the attendant definitions, wherein Y represents O.

In certain embodiments, the compounds of the present invention are represented by general structure D and the attendant definitions, wherein Y represents $H_2$.

In certain embodiments, the compounds of the present invention are represented by general structure D and the attendant definitions, wherein R represents independently for each occurrence H, alkyl, aralkyl or heteroaralkyl.

In certain embodiments, the compounds of the present invention are represented by general structure D and the attendant definitions, wherein $R_1$ represents aryl or heteroaryl.

In certain embodiments, the compounds of the present invention are represented by general structure D and the attendant definitions, wherein $R_3$ represents H, alkyl, aralkyl or heteroaralkyl.

In certain embodiments, the compounds of the present invention are represented by general structure D and the attendant definitions, wherein $R_3$ represents H, or aralkyl.

In certain embodiments, the compounds of the present invention are represented by general structure D and the attendant definitions, wherein $R_4$ is absent.

In certain embodiments, the compounds of the present invention are represented by general structure D and the attendant definitions, wherein X represents O; and Y represents O or $H_2$.

In certain embodiments, the compounds of the present invention are represented by general structure D and the attendant definitions, wherein X represents O; and Y represents O.

In certain embodiments, the compounds of the present invention are represented by general structure D and the attendant definitions, wherein X represents O; and Y represents $H_2$.

In certain embodiments, the compounds of the present invention are represented by general structure D and the attendant definitions, wherein X represents O; Y represents O or $H_2$; and $R_1$ represents aryl or heteroaryl.

In certain embodiments, the compounds of the present invention are represented by general structure D and the attendant definitions, wherein X represents O; Y represents O or $H_2$; and $R_3$ represents H, alkyl, aralkyl or heteroaralkyl.

In certain embodiments, the compounds of the present invention are represented by general structure D and the attendant definitions, wherein X represents O; Y represents O or $H_2$; and $R_3$ represents H, or aralkyl.

In certain embodiments, the compounds of the present invention are represented by general structure D and the attendant definitions, wherein X represents O; Y represents O or $H_2$; and $R_4$ is absent.

In certain embodiments, the compounds of the present invention are represented by general structure D and the attendant definitions, wherein X represents O; Y represents O or $H_2$; $R_1$ represents aryl or heteroaryl; and $R_3$ represents H, alkyl, aralkyl or heteroaralkyl.

In certain embodiments, the compounds of the present invention are represented by general structure D and the attendant definitions, wherein X represents O; Y represents O or $H_2$; $R_1$ represents aryl or heteroaryl; $R_3$ represents H, alkyl, araikyl or heteroaralkyl; and $R_4$ is absent.

In certain embodiments, the compounds of the present invention are represented by general structure D and the attendant definitions, or any of the narrower definitions, wherein said compound is a single enantiomer.

In assays based on mammalian G-protein-coupled receptors, opioid receptors or ion channels, certain compounds according to general structure D have $IC_{50}$ values less than 10 µM, more preferably less than 5 µM, and most preferably less than 1 µM.

In assays based on mammalian ion channels, certain compounds according to general structure D have $IC_{50}$ values less than 10 µM against at least one type of ion channel, more preferably less than 5 µM, and most preferably less than 1 µM.

In assays based on opioid receptors from mammalian brain, certain compounds according to general structure D have $IC_{50}$ values less than 10 µM against at least one subclass of opioid receptor, more preferably less than 5 µM, and most preferably less than 1 µM.

In assays based on mammalian ion channels and based on opioid receptors from mammalian brain, certain compounds according to general structure D have $IC_{50}$ values less than 10 µM against at least one type of ion channel and against at least one subclass of opioid receptor, more preferably less than 5 µM, and most preferably less than 1 µM.

In certain embodiments, the present invention relates to a formulation, comprising a compound represented by A, B, C, or D, and the corresponding attendant defintions; and a pharmaceutically acceptable excipient.

In certain embodiments, the present invention relates to a method of treating pain, drug addiction, or tinnitus in a mammal, comprising the step of administering to a mammal with pain, drug addiction, or tinnitus an effective amount of a formulation comprising a compound represented by A, B, C, or D, and the corresponding attendant defintions; and a pharmaceutically acceptable excipient. In certain embodiments of this method, said mammal is a primate, equine, canine or feline. In certain embodiments of this method, said mammal is a human. In certain embodiments of this method, said formulation is administered orally. In certain embodiments of this method, said formulation is administered intravenously. In certain embodiments of this method, said formulation is administered sublingually. In certain embodiments of this method, said formulation is administered ocularly. In certain embodiments of this method, said formulation is administered transdermally.

In certain embodiments, the present invention relates to ligands for G-protein-coupled receptors, opioid receptors or ion channels. Preferably the ligands of the present invention are antagonists or agonists of the G-protein-coupled receptors, opioid receptors or ion channels. In any event, the ligands of the present invention preferably exert their effect on the receptors or channels at a concentration less than about 10 micromolar, more preferably at a concentration less than about 1 micromolar, and most preferably at a concentration less than 100 nanomolar. In certain embodiments, the ligands of the present invention bind selectively to a single family of G-protein-coupled receptors, opioid receptors or ion channels. In other embodiments, the ligands of the present invention bind selectively to a subtype of receptor or channel within a family of G-protein-coupled receptors, opioid receptors or ion channels.

In certain assays based on ion channels, subject compounds have $IC_{50}$ values less than 1 µM for blocking sodium channels, more preferably less than 0.1 µM, and most preferably less than 0.05 µM. In preferred embodiments, a compound is selective for sodium channels over potassium and calcium channels, e.g., has an $IC_{50}$ for blocking sodium channels which is at least 10 times lower, preferably 100 times lower, even more preferably 1000 times lower, than its corresponding $IC_{50}$ values for potassium and calcium channels. In preferred embodiments, this selectivity is observed for all, or a majority, of the various calcium and potassium channels in the animal to be treated. In certain embodiments, the selectivity of a compound for a sodium channel renders that compound an effective therapeutic agent for an acute or chronic ailment, disease or malady.

In certain embodiments, the selectivity of a ligand for a specific family or subtype of receptor or channel renders that ligand an effective therapeutic agent for an acute or chronic ailment, disease or malady. In certain embodiments, the selectivity of a ligand for a specific family or subtype of receptor or channel consists of a binding affinity for that family or subtype of receptor or channel at least a factor of ten greater than its binding affinity for other families or subtypes of G-protein-coupled receptors, opioid receptors or ion channels. In preferred embodiments, the selectivity of a ligand for a specific family or subtype of receptor or channel consists of a binding affinity for that family or subtype of receptor or channel at least a factor of one hundred greater than its binding affinity for other families or subtypes of G-protein-coupled receptors, opioid receptors or ion channels. In certain embodiments, the selectivity of a ligand for a specific family or subtype of receptor or channel consists of a binding affinity for that family or subtype of receptor or channel at least a factor of one thousand greater than its binding affinity for other families or subtypes of G-protein-coupled receptors, opioid receptors or ion channels.

The present invention contemplates pharmaceutical formulations (see below) of the compounds of the present invention. In certain embodiments, the pharmaceutical formulations will comprise compounds of the present invention that effect only a specific family or subtype of G-protein-coupled receptors, opioid receptors or ion channels, and thereby have a therapeutic effect on an acute or chronic ailment, disease or malady that is at least in part due to biochemical or physiological processes associated with the receptor(s) or channel(s). In preferred embodiments, the pharmaceutical formulations will comprise compounds of the present invention that effect only a subtype of receptor or channel, and thereby have a therapeutic effect on an acute or chronic ailment, disease or malady that is at least in part due to biochemical or physiological processes associated with the specific subtype of receptor or channel. The Background of the Invention (see above) teaches examples of acute or chronic ailments, diseases or maladies that are caused or exacerbated by biochemical or physiological processes associated with certain G-protein-coupled receptors, opioid receptors or ion channels. One of ordinary skill in the art will be able to accumulate, by reference to the scientific literature, a more comprehensive list of acute or chronic ailments, diseases or maladies that are caused or exacerbated by biochemical or physiological processes associated with specific G-protein-coupled receptors, opioid receptors or ion channels. The present invention contemplates pharmaceutical formulations of compounds of the present invention that will be of medicinal value against the aforementioned acute or chronic ailments, diseases or maladies.

In additional embodiments, the pharmaceutical formulations will comprise compounds of the present invention that are substantially selective for sodium channels over potassium and calcium channels, and thereby have a therapeutic effect on an acute or chronic ailment, disease or malady that is at least in part due to biochemical or physiological processes associated with sodium ion channels. For example, such compounds and preparations may be used in the treatment of epilepsy, tinnitus, pain, stroke and ischemia, head trauma, neurodegenerative diseases, arrhythmia, etc., or for providing local or general anesthesia. In addition to the various conditions and applications described herein, one of ordinary skill in the art will be able to accumulate, by reference to the scientific literature (e.g., Madge, Annual Reports in Medicinal Chemistry, 33, 51-61; Taylor et al., Adv. Pharmacol., 1997, 39, 47-98), a more comprehensive list of acute or chronic ailments, diseases or maladies that are caused or exacerbated by biochemical or physiological processes associated with sodium channels. The present invention contemplates pharmaceutical formulations of compounds of the present invention that will be of medicinal value against the aforementioned acute or chronic ailments, diseases or maladies.

As antiarrhythmic drugs, the compounds are used to treat arrhythmias of the atria or ventricles of the heart in which abnormally rapid cardiac action potentials occur in either chamber or premature action potentials occur in the ventricles. Representative clinical disorders that can potentially be treated by these compounds include atrial tachycardia, atrial flutter and fibrillation, atrial arrhythmias due to re-entry, Woolf-Parkinson-White syndrome, ventricular premature systole (also called premature ventricular contractions, PVCs), ventricular tachycardia and fibrillation, and sudden cardiac death. Antiarrhythmic drugs may also be administered to patients following a myocardial infarction ("heart attack") or to patients with congestive heart failure or cardiomyopathy in order to prevent arrhytnias. Desired clinical end points for treatment of these disorders include reduction of heart rate, regularization of ventricular rhythms, prevention of premature ventricular systoles, and prevention of ventricular fibrillation and sudden cardiac death. The efficacy of the subject compounds in treatment of arrhythmias may be first established in animal models of cardiac arrhythmia including arrhythmias initiated by electrical stimulation, focal myocardial injury, and ischemic injury followed by electrical stimulation or coronary arterial occlusion.

As anticonvulsant drugs, the compounds are used to treat epileptic seizures including grand mal, temporal lobe, and partial complex seizures. Desired clinical end points include reduction of frequency and severity of seizures. Efficacy may be demonstrated in animal models of seizure including maximal electroshock seizures, seizures due to kainic acid lesions of the hippocampus, seizures due to "kindling" of the amygdala in rat, and seizures induced by topical alumina cream on the cortical surface of monkeys.

As local anesthetic drugs and analgesics, the compounds are used to provide relief from pain in dentistry and localized surgical and medical procedures. They may be administered by localized injection or by intrathecal or epidural infision. These therapeutic applications may be tested by measurement of block of sensory nerve conduction by the compounds, and by block of pain responses, using standard small animal tests of pain transmission including the hot plate and tail flick tests, the induction of neuromas by surgical section of peripheral nerves, and the induction of pain by cutaneous pressure.

For the treatment of tiunitus, the compounds are used to ameliorate the false perception of sound, such as a ringing sound, in a patient, in some cases resulting in an improvement in hearing. Tests for efficacy may be performed in humans after obtaining data indicative of the compound's safety, or an animal model may be employed (Zhang, et al. Neurosci Lett 1998, 250(3), 197-200).

As neuroprotective agents, the compounds are used to prevent neuronal damage and death during and follow ischemic episodes associated with cardiac surgery, cerebral aneurysm, and stroke. Therapeutic value may be assessed from retention and recovery of normal neurological status following stroke. Efficacy in neuroprotection may be assessed in animal models of stroke involving experimental occlusion of major cerebral arteries such as the middle cerebral artery occlusion model.

Biochemical Activity at Cellular Receptors, and Assays to Detect that Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for μ-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315-21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and factory neuron channels [see Altenhafan W. et al. (1991) Proc. Natl. adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50-150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694-697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido)fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific MRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<-> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<-> and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403-410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330-334); the rat alpha3 subunit (Boulter et al. (1986) Nature 319:368-374); the rat alpha 4 subunit (Goldman et al. (1987) cell 48:965-973); the rat alpha 5 subunit (Boulter et al. (1990) J. Biol. Chem. 265:4472-4482); the rat beta 2 subunit (Deneris et al. (1988) Neuron 1:45-54); the rat beta 3 subunit (Deneris et al. (1989) J. Biol. Chem. 264: 6268-6272); the rat beta 4 subunit (Duvoisin et al. (1989) Neuron 3:487-496); combinations of the rat alpha subunits, beta subunits and alpha and beta subunits; GABA receptors (e.g., the bovine alpha 1 and beta 1 subunits (Schofield et al. (1987) Nature 328:221-227); the bovine alpha 2 and alpha 3 subunits (Levitan et al. (1988) Nature 335:76-79); the gamma—subunit (Pritchett et al. (1989) Nature 338:582-585); the beta 2 and beta 3 subunits (Ymer et alo (1989) EMBO J. 8:1665-1670); the delta subunit (Shivers, B. D. (1989) Neuron 3:327-337); and the like); glutamate receptors (e.g., receptor isolated from rat brain (Hollmann et al. (1989) Nature 342:643-648); and the like); adrenergic receptors (e.g., human beta 1 (Frielle et al. (1987) Proc. Natl. Acad. Sci. 84:7920-7924); human alpha 2 (Kobilka et al. (1987) Science 238:650-656); hamster beta2 (Dixon et al. (1986) Nature 321:75-79); and the like); dopamine receptors (e.g., human D2 (Stormann et al. (1990) Molec. Pharm. 37:1-6); rat (Bunzow et al. (1988) Nature 336:783-787); and the like); NGF receptors (e.g., human NGF receptors (Johnson et al. (1986) Cell 47:545-554); and the like); serotonin receptors (e.g., human 5HT1a (Kobilka et al. (1987) Nature 329:75-79); rat 5HT2 (Julius et al. (1990) PNAS 87:928-932); rat 5HT1c (Julius et al. (1988) Science 241:558-564); and the like).

Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101).

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477-485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In vivo Activity Assays

Various experimental procedures, well known in the art, are useful in the present invention to assess the analgesic effect of compounds, such as the "tail flick" and "hot plate" tests. The "tail flick" test can be performed by applying a noxious thermal stimulus to the rat's tail and determining the time until the nociceptive tail flick occurs. Analgesia is demonstrated by an increase in time to occurrence of a tail flick response. The "hot plate" test is similarly performed, except that the noxious thermal stimulus is applied to the rat's paws.

An experimental procedure, well known in the art, useful in the present invention to assess the ability of compounds to cause respiratory depression is to monitor blood gases. This method employees measuring the partial pressures of oxygen and carbon dioxide in blood samples taken from animals following compound administration. A decrease in the partial pressures of oxygen and an increase in the partial pressure of carbon dioxide may be indicative of respiratory depression.

An experimental procedure, well known in the art, useful in the present invention to assess the ability of compounds to cause inhibition of gastrointestinal motility is the "charcoal meal test". This method measures the propulsion of intestinal contents following administration of test compounds. A decrease in the propulsion of intestinal contents may be indicative of inhibition of gastrointestinal motility.

Various experimental procedures, well known in the art, are useful in the present invention to assess the ability of compounds to cause tolerance. Tolerance can be defined as a condition characterized by unresponsiveness or decreased responsiveness following prolonged or multiple exposure to a compound compared to the responsiveness demonstrated upon initial exposure.

Various experimental procedures, well known in the art, are useful in the present invention to assess the ability of compounds to cause physical dependence. In the present invention, the ability of test compounds to cause physical dependence was accessed by giving animals escalating doses of test compounds for five days. After the final dose the animals were given naloxone, an opioid antagonist and observed for behavioral signs of dependence, such as vertical jumping.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetrascetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound selected from the group consisting of the compounds represented by A, B, C, D, E, and F, and any of the attendant sets of definitions. In certain embodiments, an aforementioned formulation renders orally bioavailable a compound represented by A, B, C, D, E, or F, and any of the attendant sets of definitions.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuzyl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffets, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811-5814; Valerio et al. (1991) Anal Biochem 197:168-177; Bray et al. (1991) Tetrahedron Lett 32:6163-6166).

C) Divide-Couple-Recombine

In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of [1-(S)-(1-Benzyl-pyrrolidin-3-(R)-yl-carbamoyl)-2,2-dimethyl-propyl]-carbamic acid tert-butyl ester (1a)

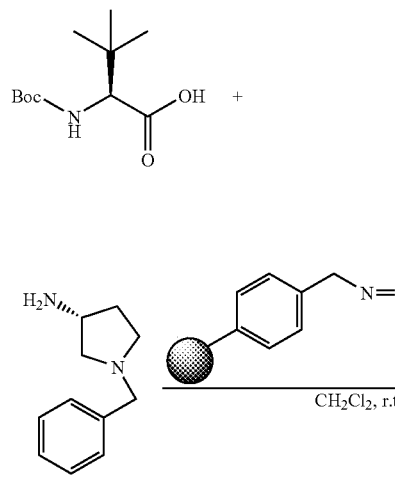

1a

To a solution of N-α-Boc-L-α-tert-butylglycine (2.0 g, 8.65 mmole) in dichloromethane (20 mL) was added 3R-(−)-1-Benzyl-3-(methylamino)pyrrolidine (1.68 g, 9.51 mmole) followed by N-cyclohexylcarbodiimide, N'-methyl polystyrene resin (loading=1.5 mmole/g; 6.92 g, 10.38 mmole). This mixture was agitated in a sealed vessel on an orbital shaker for 18 h, and then the slurry was gravity filtered. The resin was washed with dichloromethane and methyl alcohol, and then the solvent was removed by rotary evaporation. The organic residue was purified by flash chromatography on silica gel, eluting with dichloromethane/2.0 M ammonia in ethyl alcohol (96:4) to give 1a (1.15 g, 34%) as a pale yellow solid.

EXAMPLE 2

Synthesis of [1-(S)-(1-Benzyl-pyrrolidin-3-(S)-ylcarbamoyl-2,2-dimethyl-propyl]-carbamic acid tert-butyl ester (1b)

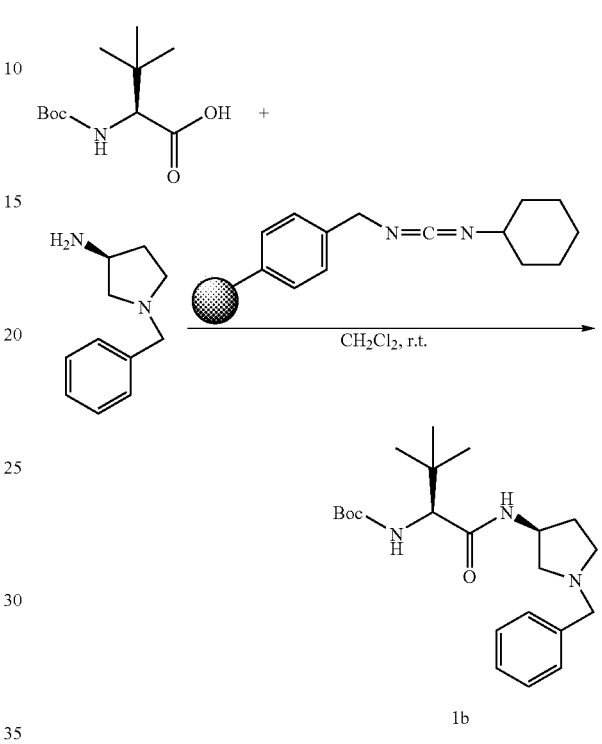

1b

Compound 1b was prepared from N-α-Boc-L-α-tert-butylglycine and 3S-(−)-1-Benzyl-3-(methylamino)pyrrolidine, using the method described in Example 1.

EXAMPLE 3

Synthesis of 3-(S)-(1-Benzyl-piperidin-4-ylcarbamoyl)-3,4-dihydro-1H-isoquinoline-2-carboxylic acid tert-butyl ester (1c)

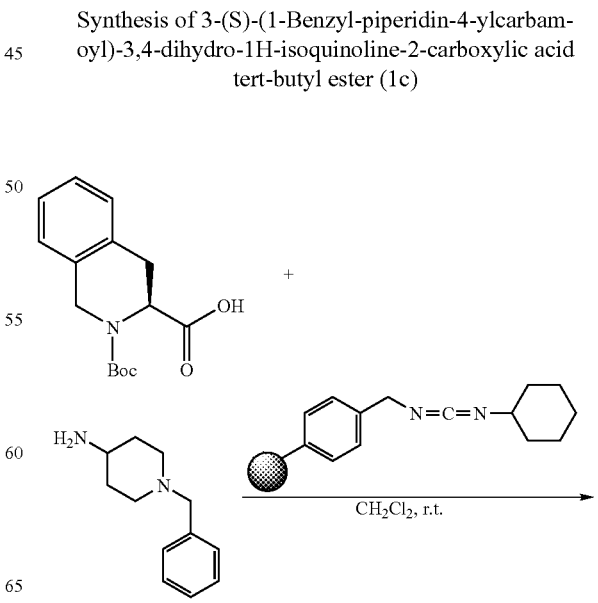

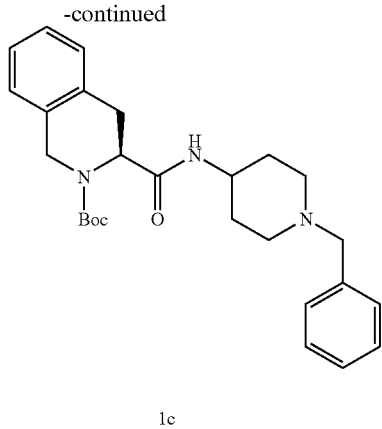

1c

Compound 1c was prepared from N-Boc-L-1,2,3,4-tetrahydroisoquinoline-3-carboxylic acid and 4-amino-1-benzylpiperidine, using the method described in Example 1.

EXAMPLE 4

3-[Benzyl-(2-dimethylamino-ethyl)-carbamoyl]-3,4-dihydro-1H-isoquinoline-2-carboxylic acid tert-butyl ester (1d)

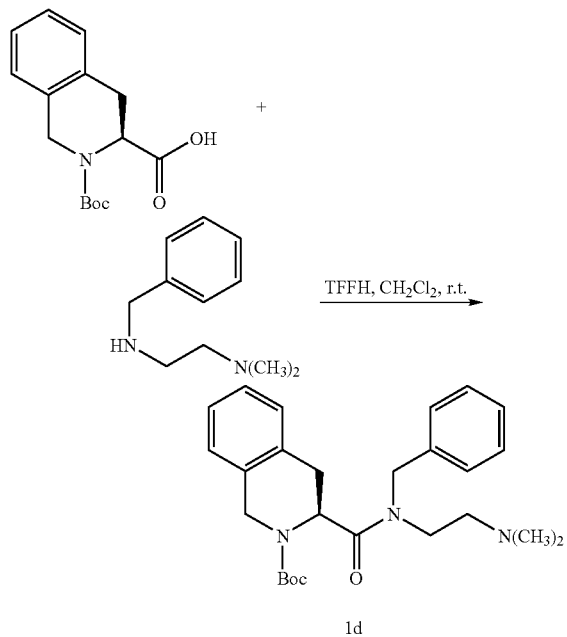

1d

To a solution of N-Boc-L-1,2,3,4-tetrahydroisoquinoline-3-carboxylic acid (2.0 g, 7.2 mmole) in dichloromethane (20 mL) was added TFFH (1.91 g, 7.2 mmole). The mixture was cooled to 0° C. and N'-benzyl-N,N-dimethylethylenediamine (2.57 g, 14.4 mmole) was added to the reaction. The reaction was allowed to warm to room temperature and stirred for 6 h. The reaction was then quenched with water (20 mL), and the organic layer was dried over anhydrous sodium sulfate, filtered and concentrated. The organic residue was purified by flash chromatography on silica gel, eluting with dichloromethane/2.0 M ammonia in ethyl alcohol (96:4) to give 1d (0.81 g, 26%) as a pale yellow oil.

EXAMPLE 5

2-(S)-Amino-N-(1-benzyl-pyrrolidin-3-(R)-yl)-3,3-dimethyl-butyramide (2a)

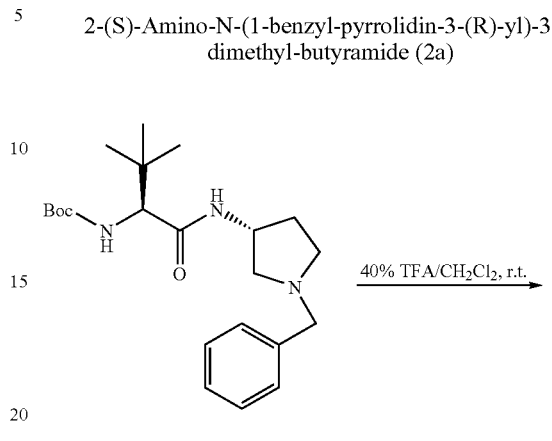

1a

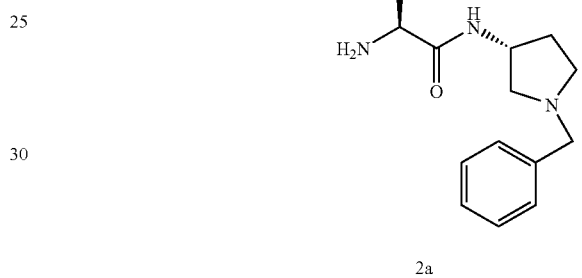

2a

A solution of 1a (0.80 g, 2.06 mmole) in 40% trifluoroacetic acid/dichloromethane (15 mL) was stirred at room temperature for 4 h. The solvent was removed by rotary evaporation, and the resulting organic residue was carefully partitioned between dichloromethane and a saturated solution of sodium bicarbonate (30 mL each). The organic extract was dried over anhydrous sodium sufate, filtered, and concentrated to give 2a as a light brown oil. This amine was used without further purification.

EXAMPLE 6

2-(S)-Amino-N-(1-benzyl-pyrrolidin-3-(S)-yl)-3,3-dimethyl-butyramide (2b)

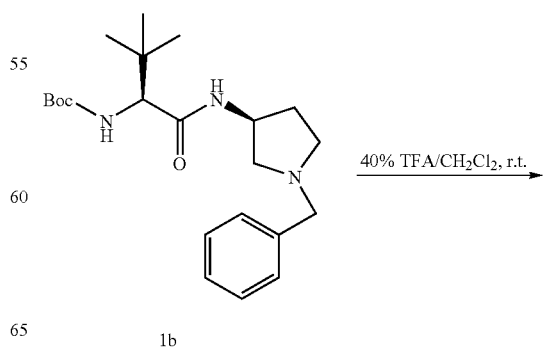

1b

-continued

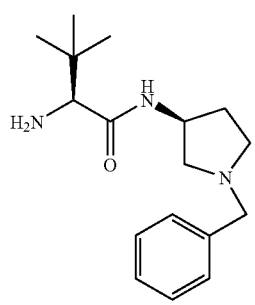

2b

Compound 2b was prepared from compound 1b, using the method described in Example 5.

EXAMPLE 7

1,2,3,4-Tetrahydro-isoquinoline-3-(S)-carboxylic acid (1-benzyl-piperidin-4-yl)-amide (2c)

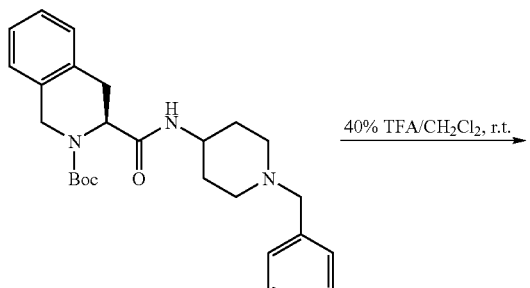

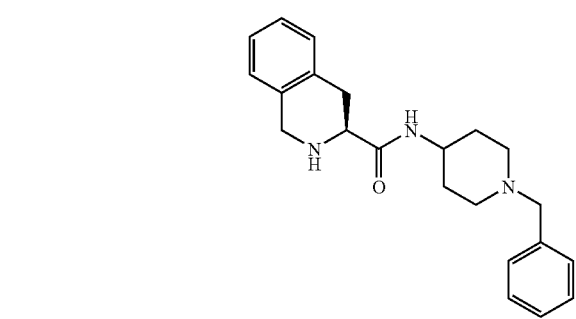

2c

Compound 2c was prepared from compound 1c, using the method described in Example 5.

EXAMPLE 8

1,2,3,4-Tetrahydro-isoquinoline-3-(S)-carboxylic acid benzyl-(2-dimethylamino-ethyl)-amide (2d)

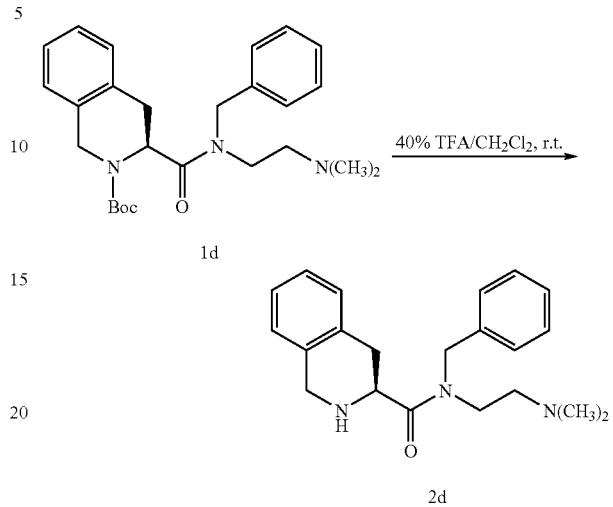

Compound 2d was prepared from compound 1d, using the method described in Example 5.

EXAMPLE 9

N-(1-Benzyl-pyrrolidin-3-(R)-yl)-3,3-dimethyl-2-(S)-[3-(3-trifluoromethyl-phenyl)-ureido]-butyramide (3a)

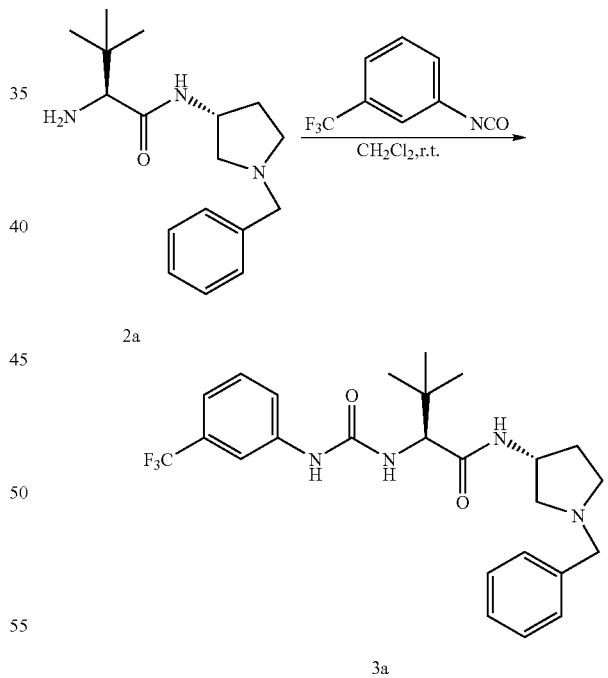

3-(Trifluoromethyl)phenyl isocyanate (0.093 g, 0.50 mmole) was slowly added to a solution of 2a (0.12 g, 0.42 mmole) in dichloromethane (20 mL) at 0° C. The solution was allowed to warm to room temperature and stirred for 18 h. The reaction was then quenched with water (20 mL), and the organic layer was dried over anhydrous sodium sulfate, filtered and concentrated. The organic residue was purified by flash chromatrographey on silica gel, eluting with dichloromethane/2.0 M ammonia in ethyl alcohol (96:4) to give 3a (0.045 g, 34%) as a white solid; MS (EI)=476 (M+).

EXAMPLE 10

N-(1-Benzyl-pyrrolidin-3-(S)-yl)-3,3-dimethyl-2-(S)-[3-(3-trifluoromethyl-phenyl)-ureido]-butyramide(3b)

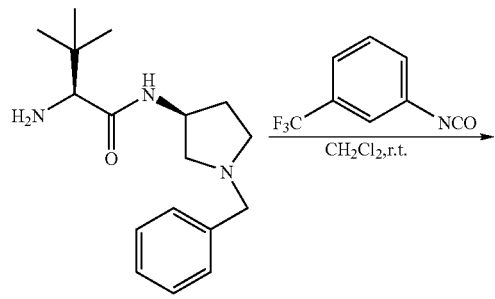

2b

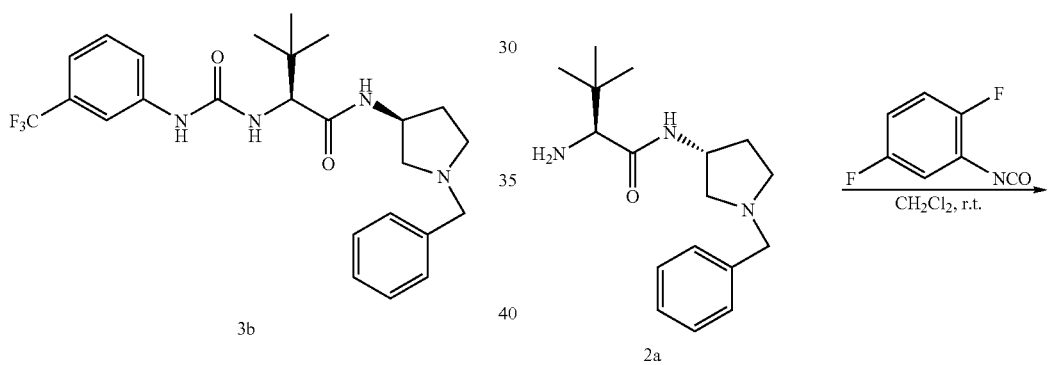

3b

Compound 3b was prepared from 3-(trifluoromethyl)phenyl isocyanate and compound 2b, using the method described in Example 9. MS (EI)=476 (M+).

EXAMPLE 11

N-(1-Benzyl-pyrrolidin-3-(S)-yl)-2-(S)-[3-(2,5-difluoro-phenyl)-ureido]-3,3-dimethyl-butyramide (3c)

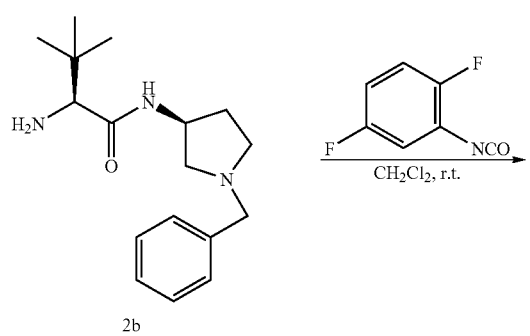

2b

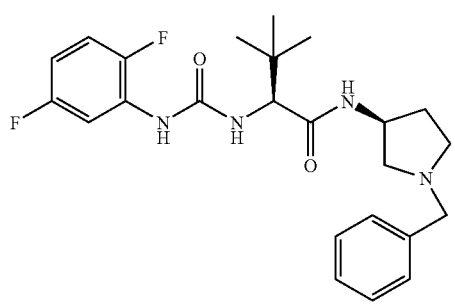

3c

Compound 3c was prepared from 2,5-difluorophenyl isocyanate and compound 2b, using the method described in Example 9. MS (EI)=444 (M+).

EXAMPLE 12

N-(1-Benzyl-pyrrolidin-3-(R)-yl)-2-(S)-[3-(2,5-difluoro-phenyl)-ureido]-3,3-dimethyl-butyramide (3d)

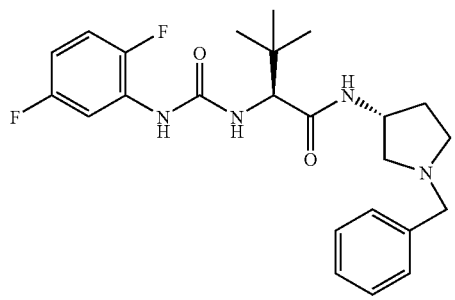

2a

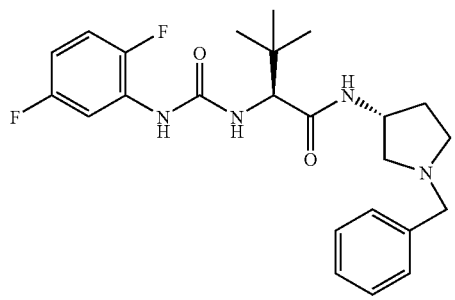

3d

Compound 3d was prepared from 2,5-difluorophenyl isocyanate and compound 2a using the method described in Example 9. MS (EI)=444 (M+).

EXAMPLE 13

3,4-Dihydro-1H-isoquinoline-2,3-dicarboxylic acid 3-(S)-[(1-benzyl-piperidin-4-yl-amide]2-[(3-trifluoromethyl-phenyl)-amide] (3e)

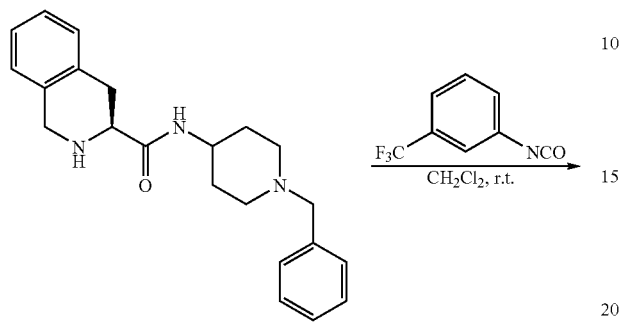

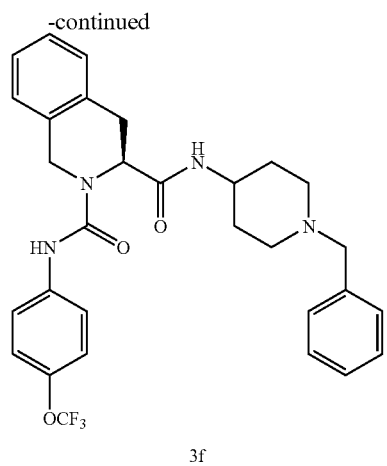

Compound 3e was prepared from 3-(trifluoromethyl)phenyl isocyanate and compound 2c, using the method described in Example 9. MS (EI)=536 (M+).

EXAMPLE 14

3,4-Dihydro-1H-isoquinoline-2,3-dicarboxylic acid 3-(S)-[(1-benzyl-piperidin-4-yl)-amide] 2-[(4-trifluoromethoxy-phenyl)-amide] (3f)

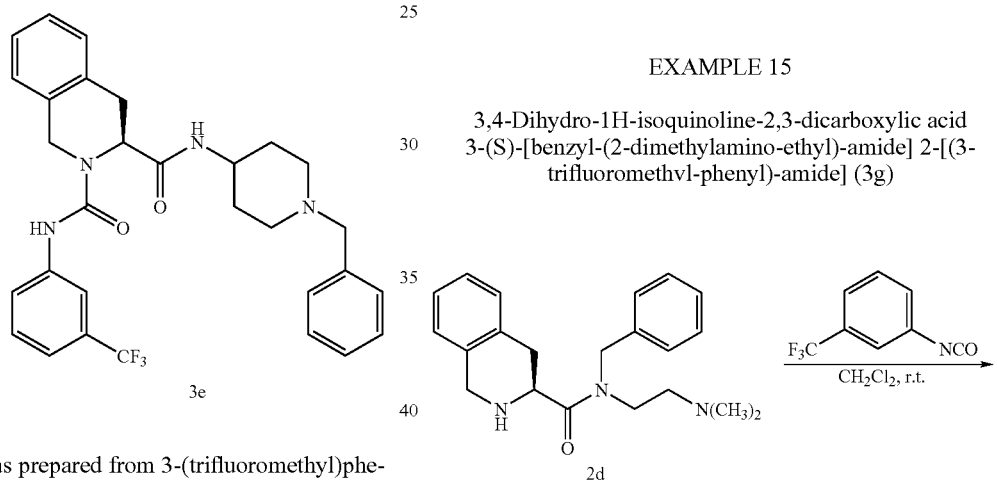

Compound 3f was prepared from 4-(trifluoromethoxy) phenyl isocyanate and compound 2c, using the method described in Example 9.

EXAMPLE 15

3,4-Dihydro-1H-isoquinoline-2,3-dicarboxylic acid 3-(S)-[benzyl-(2-dimethylamino-ethyl)-amide] 2-[(3-trifluoromethvl-phenyl)-amide] (3g)

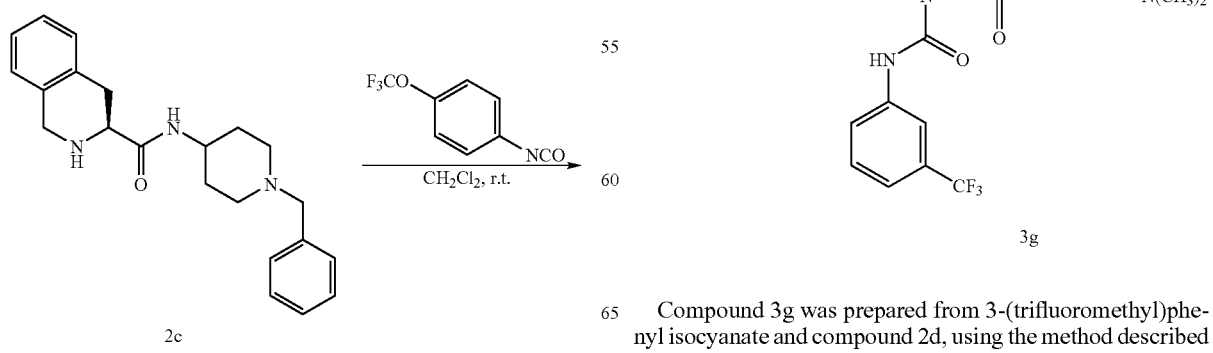

Compound 3g was prepared from 3-(trifluoromethyl)phenyl isocyanate and compound 2d, using the method described in Example 9.

EXAMPLE 16
3,4-Dihydro-1H-isoquinoline-2,3-dicarboxylic acid 3-(S)-[benzyl-(2-dimethylamino-ethyl)-amide] 2-[(4-trifluoromethoxy-phenyl)-amide] (3h)
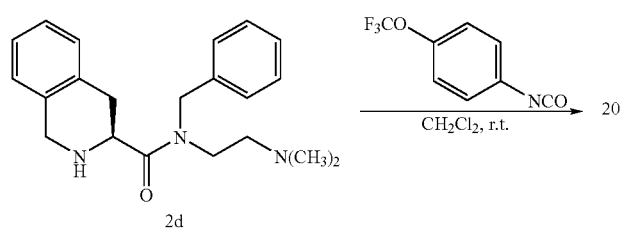
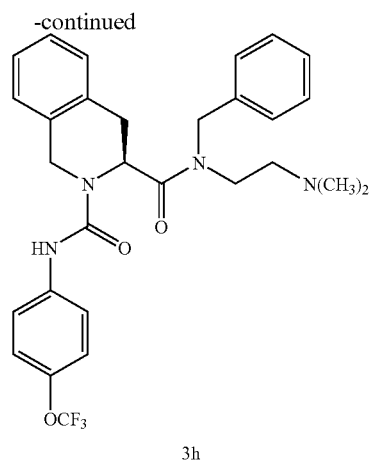
Compound 3h was prepared from 4-(trifluoromethoxy) phenyl isocyanate and compound 2d, using the method described in Example 9.
EXAMPLE 17
Preparation of 4 and 5
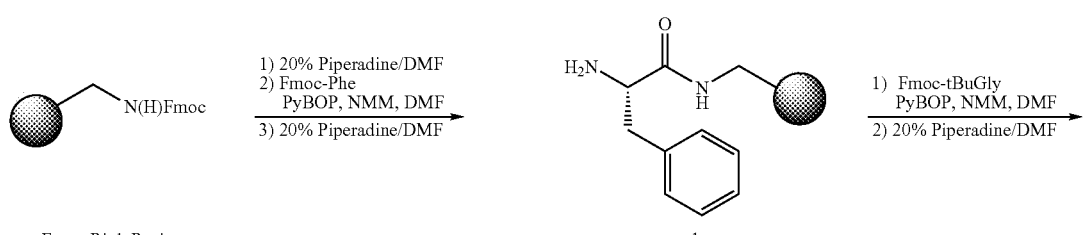
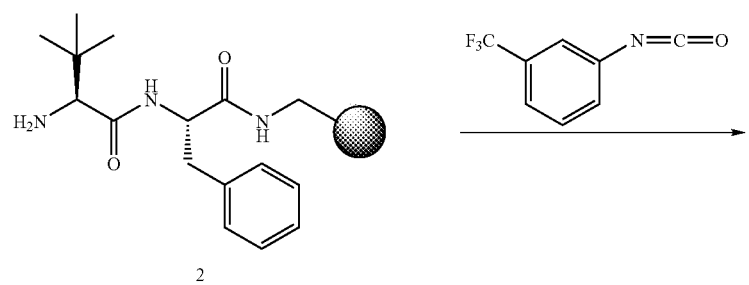

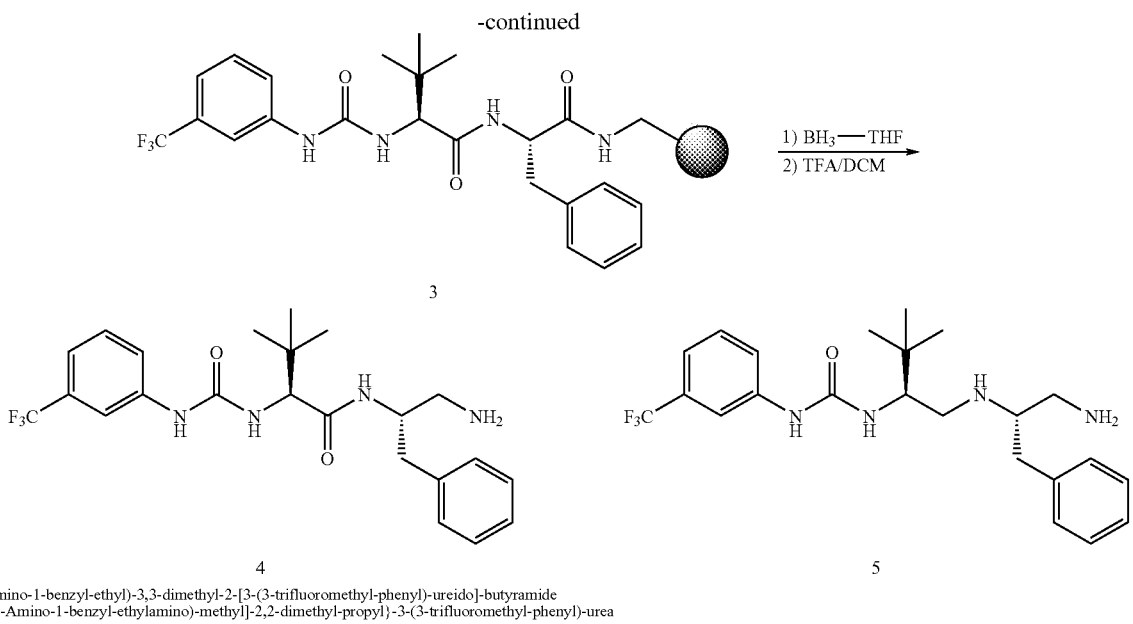

4: N-(2-Amino-1-benzyl-ethyl)-3,3-dimethyl-2-[3-(3-trifluoromethyl-phenyl)-ureido]-butyramide
5: 1-{1-[(2-Amino-1-benzyl-ethylamino)-methyl]-2,2-dimethyl-propyl}-3-(3-trifluoromethyl-phenyl)-urea Fmoc-Rink Resin (4.0 g, 2.32 mmol) was deprotected by agitating the resin with 20% piperidine in DMF (40 mL) for 30 minutes at room temperature. To the free amine resin was then added a solution of PyBOP (12.1 g, 23.2 mmol), Fmoc-Phe (9.0 g, 23.2 mmol) and NMM (2.6 mL, 23.2 mmol) in DMF (40 mL) and the suspension allowed to agitate at room temperature for 24 hours. The resulting resin was washed with DMF, CH$_2$Cl$_2$ and MeOH before treating with a solution of 20% piperidine in DMF (40 mL) at room temperature for 30 minutes. The resulting resin 1 was washed with DMF, CH$_2$Cl$_2$ and MeOH. To resin 1 was then added a solution of PyBOP (12.1 g, 23.2 mmol), Fmoc-t-BuGly (8.20 g, 23.2 mmol) and NMM (2.6 mL, 23.2 mmol) in DMF (40 mL) and the suspension allowed to agitate at room temperature for 24 hours. After washing with DMF, CH$_2$Cl$_2$ and MeOH, the Fmoc group was removed by treating with a solution of 20% piperidine in DMF (40 mL) at room temperature for 30 minutes. The resulting resin 2 was washed with DMF, CH$_2$Cl$_2$ and MeOH. To a suspension of resin 2 in CH$_2$Cl$_2$ (40 mL) was added α,α,α-trifluoro-m-tolyl isocyanate (3.19 mL, 23.2 mmol) and the resulting suspension allowed to agitate at room temperature for 18 hours. The resin was then washed thoroughly with DMF, CH$_2$Cl$_2$, and MeOH to provide 3. To resin 3 (800 mg, 0.464 mmol) was added a 1.0 M solution of BH$_3$-THF (12.0 mL, 12.0 mmol) and the suspension allowed to agitate at 50° C. for 18 hours. The suspension was then allowed to cool to 0° C. before quenching the excess reagent with MeOH. After removal of the solvent, the resin was treated with three equivalents of a 0.06 M solution of DBU in 9:1 NMP:MeOH and the resulting suspension allowed to shake at room temperature for six hours. The solvent was then removed and the resin washed with CH$_2$Cl$_2$ to provide a mixture of 4 and 5. This mixture was treated with a 1:1 solution of TFA in CH$_2$C$_2$ (8 mL) at room temperature for one hour to release the desired products from the resin. The resulting solution of 4 and 5 was drained from the resin, the resin washed with copious CH$_2$Cl$_2$ and the solution concentrated in vacuo. The products were separated using reverse phase HPLC (6:4, acetonitrile:water) to provide, after lyophilizing, pure 4 and 5 (as their corresponding TFA salts) as fluffy powders. 4: LRMS calculated for C$_{23}$H$_{29}$F$_3$N$_4$O$_2$ 450.22, found 450.22. 5: LRMS calculated for C$_{23}$H$_{31}$F$_3$N$_4$O 432.24, found 436.07.

EXAMPLE 18

Preparation of 8 and 9

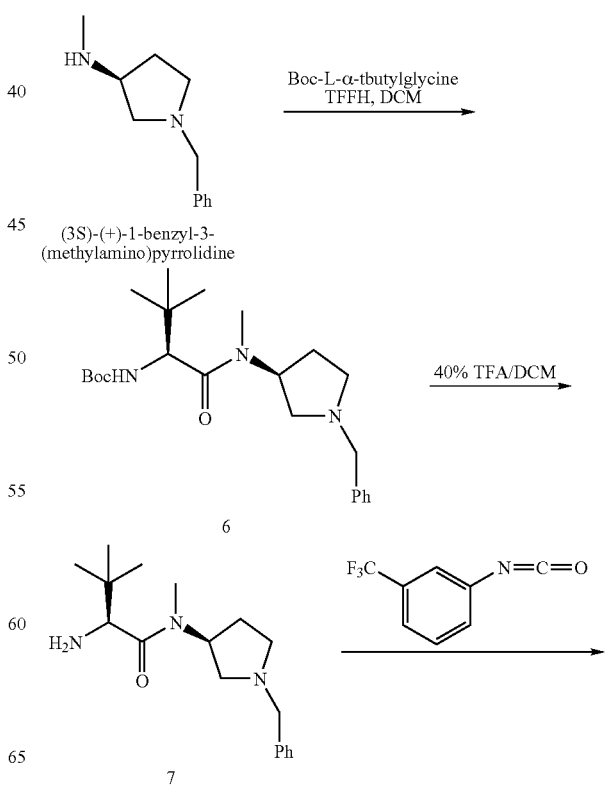

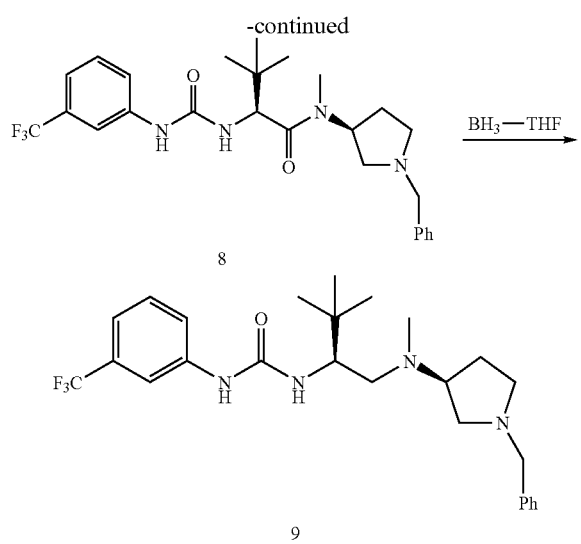

8: N-(1-Benzyl-pyrrolidin-3-yl)-3,3,N-trimethyl-2-[3-(3-trifluoromethyl-phenyl)-ureido]-butyramide
9: 1-(1-{[(1-Benzyl-pyrrolidin-3-yl)-methyl-amino-]-methyl}-2,2-dimethyl-propyl)-3-(3-trifluoromethyl-phenyl)-urea To a stirring solution of Boc-L-α-tbutylglycine (1.21 g, 5.25 mmol) in DCM (20 mL) at room temperature was added TFFH (tetramethylfluoroformamidinium hexafluorophosphate, 1.39 g, 5.25 mmol) and the mixture allowed to stir for ten minutes until a clear, homogeneous solution resulted. Next, the solution was cooled to 0° C. (at which time a white precipitate formed) and (3S)-(+)-1-benzyl-3-(methylamine) pyrrolidine (2.0 g, 10.5 mmol) was added. After stirring at 0° C. for five minutes, the reaction was allowed to warm to room temperature and continue for one and one half hours. The reaction was then extracted between DCM and water, the organic layer separated, dried (MgSO$_4$), filtered and concentrated in vacuo. The resulting residue was purified by flash column chromatography using silica gel with a gradient of 2 to 5% of a 2.0 M solution of NH$_3$ in EtOH/DCM to provide pure 6 (1.983 g, 94%). LRMS calculated for $C_{23}H_{37}N_3O_3$ 403.28, found 403.86.

Boc-protected amine 6 (1.96 g, 4.86 mmol) was treated with a solution of 40% TFA in DCM (20 mL) and the solution allowed to stir at room temperature for two hours. The reaction solution was then concentrated in vacuo, the residue dissolved in DCM and washed three times with a saturated aqueous solution of NaHCO$_3$. The organic layer was dried (Na$_2$SO$_4$), filtered and concentrated in vacuo to provide free amine 7 (1.015 g, 69%). LRMS calculated for $C_{18}H_{29}N_3O$ 303.23, found 303.94.

To a solution of 7 (496 mg, 1.64 mmol) in DCM (5 mL) at room temperature was added α,α,α-trifluoro-m-tolyl isocyanate (271 μL, 1.97 mmol) and the reaction allowed to stir for seventeen hours. Next, one equivalent of tris-(2-aminoethyl)-amine polystyrene HL resin was added to absorb the excess isocyanate and the suspension allowed to stir for two hours before filtering to remove the resin and concentrating the resulting solution in vacuo. The resulting residue was then purified by flash column chromatography using silica gel and 3% 2.0 M NH$_3$ in EtOH/DCM to provide pure 8 (456 mg, 57%). LRMS calculated for $C_{26}H_{33}F_3N_4O_2$ 490.26, found 490.

To a solution of 8 (55 mg, 0.112 mmol) in THF (0.51 mL) was added 1.0 M BH$_3$-THF (340 μL, 0.340 mmol) and the reaction heated to 50° C. for 22 hours. The reaction temperature was then increased to 80° C. and the reaction allowed to continue for an additional 24 hours. After cooling to room temperature, 2 M aqueous HCl (approx. 1 mL) was added to the reaction and the solution allowed to stir for one and one half hours. Next, the solution was basified with aqueous 2 M NaOH and extracted with DCM. The combined organic extracts were dried (MgSO$_4$), filtered and concentrated in vacuo. The resulting residue was then purified by flash column chromatography using silica gel and a gradient of 2 to 5% 2.0 M NH$_3$ in EtOH/DCM to provide pure 9 (15 mg, 28%). LRMS calculated for $C_{26}H_{35}F_3N_4O$ 476.28, found 476.03.

EXAMPLE 19

Preparation of 10 and 11

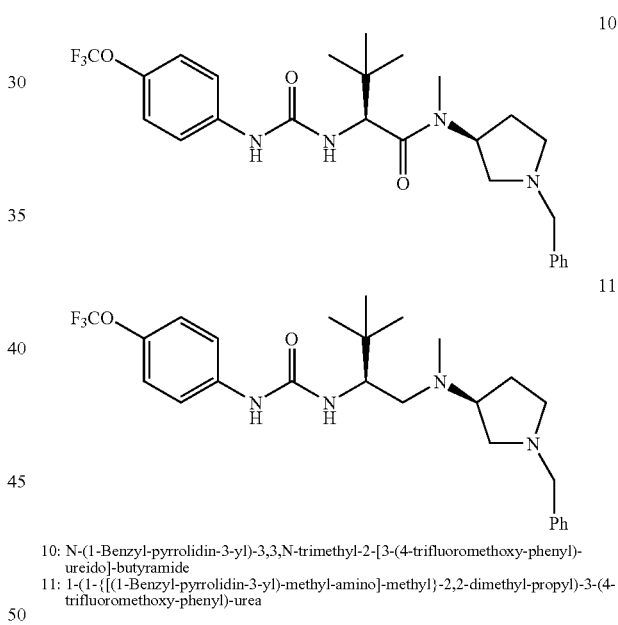

10: N-(1-Benzyl-pyrrolidin-3-yl)-3,3,N-trimethyl-2-[3-(4-trifluoromethoxy-phenyl)-ureido]-butyramide
11: 1-(1-{[(1-Benzyl-pyrrolidin-3-yl)-methyl-amino]-methyl}-2,2-dimethyl-propyl)-3-(4-trifluoromethoxy-phenyl)-urea The method of Example 18 was used with 4-trifluoromethoxyphenyl isocyanate instead of α,α,α-trifluoro-m-tolyl isocyanate.

Preparation of 10: 7 (496 mg, 1.64 mmol), 4-trifluoromethoxyphenyl isocyanate (0.297 mL, 1.97 mmol), DCM (5 mL). Purification by flash column chromatography using 3% 2M NH$_3$ in EtOH/DCM provided the desired 10 (444 mg, 53%). LRMS calculated for $C_{26}H_{33}F_3N_4O_3$ 506.25, found 507.

Preparation of 11: 10 (50 mg, 0.099 mmol), 1.0 M BH$_3$-THF (0.296 mL, 0.296 mmol), THF (0.5 mL). Purification by flash column chromatography using a gradient of 2 to 5% 2M NH$_3$ in EtOH/DCM provided the desired 11 (8 mg, 15%) .LRMS calculated for $C_{26}H_{35}F_3N_4O_2$ 492.27, found 492.84.

EXAMPLE 20

{1-(S)-[Benzyl-(2-dimethylamino-ethyl)-carbamoyl]-2-methyl-propyl}-carbamic acid tert-butyl ester (12)

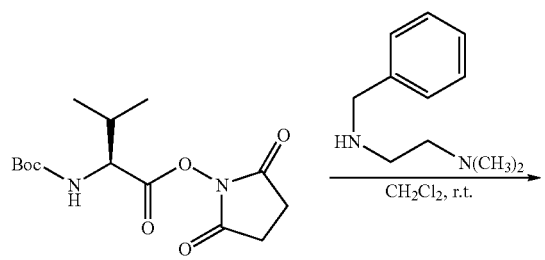

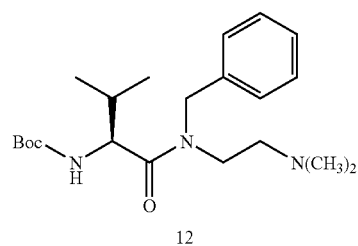

To a solution of N-α-Boc-L-valine-N'-hydroxysuccinimide ester (2.0 g, 6.36 mmole) in dichloromethane (20 mL) at 0° C. was added N'-benzyl-N,N-dimethylethylenediamine (1.25 g, 7.00 mmole) and triethylamine (0.71 g, 7.00 mmole. The reaction was allowed to warm to room temperature and stirred for 6 h. The reaction was then quenched with water (20 mL), and the organic layer was washed with water (2×). The organic layer was dried over anhydrous sodium sulfate, filtered and concentrated by rotary evaporation. The organic residue was purified by flash chromatography on silica gel, eluting with dichloromethane/2.0 M ammonia in ethyl alcohol (96:4) to give 12 (1.28 g, 53%) as a white solid.

EXAMPLE 21

2-Amino-N-benzyl-N-(2-dimethylamino-ethyl)-3-methyl-butyramide (13)

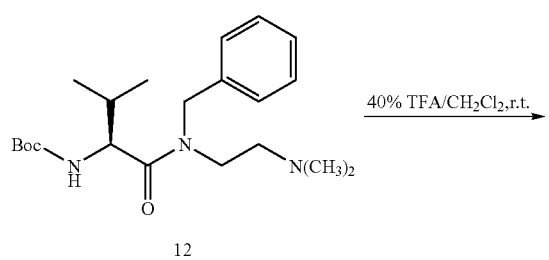

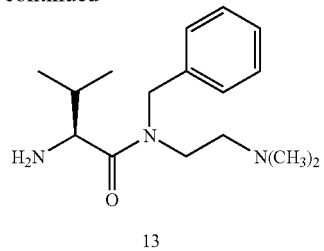

A solution of 12 (1.15 g, 2.92 mmole) in 40% trifluoroacetic acid/dichloromethane (15 mL) was stirred at room temperature for 4 h. The solvent was removed by rotary evaporation, and the resulting organic residue was carefully partitioned between dichloromethane and a saturated solution of sodium bicarbonate (30 mL each). The organic extract was dried over anhydrous sodium sufate, filtered, and concentrated to give 13 (0.80 g, 95%) as a light brown oil. This amine was used in the next step without further purification.

EXAMPLE 22

N-Benzyl-N-(2-dimethylamino-ethyl)-3-methyl-2-(S)-[3-(4-trifluoromethoxy-phenyl)-ureido]-butyramide (14a)

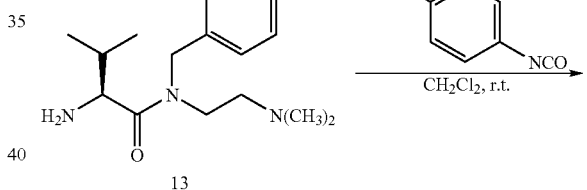

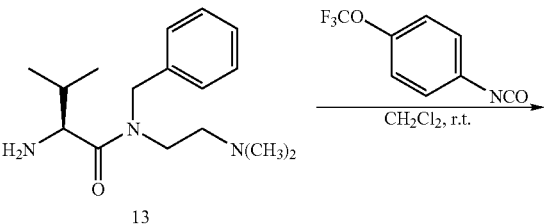

4-(Trifluoromethoxy)phenyl isocyanate (0.18 g, 0.86 mmole) was slowly added to a solution of 13 (0.20 g, 0.72 mmole) in dichloromethane (20 mL) at 0° C. The solution was allowed to warm to room temperature and stirred for 18 h. The reaction was then quenched with water (20 mL), and the organic layer was dried over anhydrous sodium sulfate, filtered and concentrated by rotary evaporation. The organic residue was purified by flash chromatograpthey on silica gel, eluting with dichloromethane/2.0 M ammonia in ethyl alcohol (96:4) to give 14a (0.24 g, 69%) as a white solid; MS (EI)=480 (M+).

EXAMPLE 23

N-Benzyl-N-(2-dimethylamino-ethyl)-2-(S)-[3-(4-fluorophenyl)-ureido]-3-methyl-butyramide (14b)

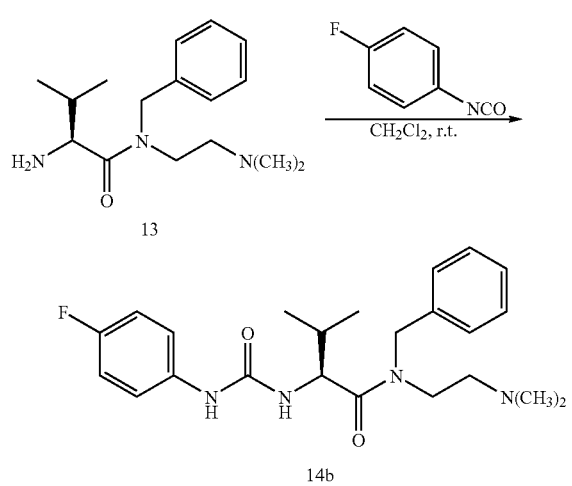

Compound 14b was prepared from 4-fluorophenyl isocyanate and compound 13, using the method described in Example 22. MS (EI)=414 (M+).

EXAMPLE 24

N-Benzyl-N-(2-dimethylamino-ethyl)-3-methyl-2-(S)-[3-(4-trifluoromethyl-phenyl)-ureido]-butyramide (14c)

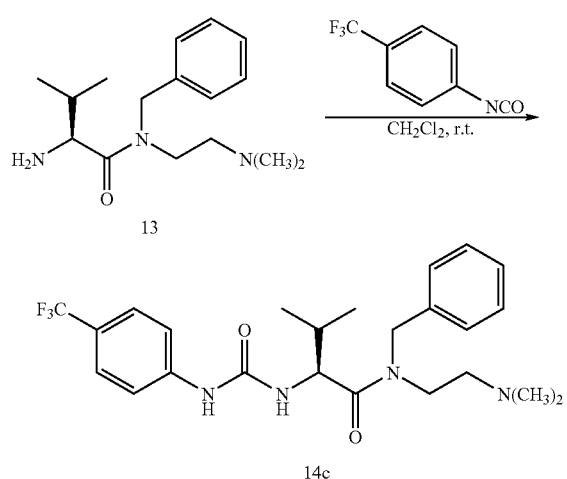

Compound 14c was prepared from 4-(trifluoromethyl) phenyl isocyanate and compound 13, using the method described in Example 22. MS (EI)=464 (M+).

EXAMPLE 25

N-(1-Benzyl-2-oxo-2-piperazin-1-yl-ethyl)-3,3-dimethyl-2-[3-(3-trifluoromethylphenyl)-ureido]-butyramide (15)

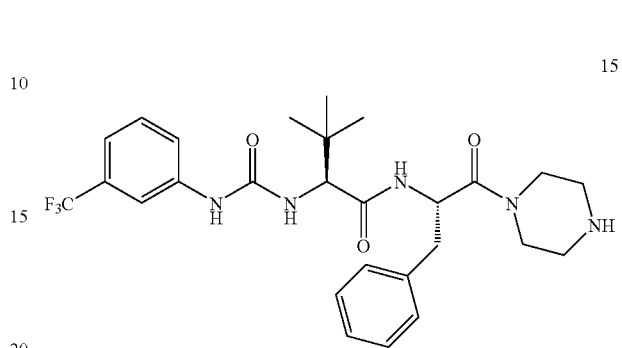

The method of Example 17 was used with the following exceptions: In place of Fmoc-Rink Resin, Wang resin (25 g, 17.5 mmol) was treated with 1,1'-carbonyldiimidazole (19.9 g, 0.122 mol) in tetrahydrofuran (330 mL) to provide the imidazolide resin. This was then allowed to react with piperazine (15.1 g, 0.175 mol) in tetrahydrofuran (400 mL) to generate the piperazine-functionalized resin. This resin was then coupled to Fmoc-Phe and carried through the synthesis as in Example 17 (using the same stoichiometry and reagents). The final step of cleavage from the resin was performed without the preceeding borane reduction step. 15: LRMS calculated for $C_{27}H_{34}F_3N_5O_3$ 533.26, found 533.54.

EXAMPLE 26

N-Benzyl-N-(2-dimethylamino-ethyl)-3,3-dimethyl-2-[3-(3-trifluoromethyl-phenyl)-ureido]-butyramide (16)

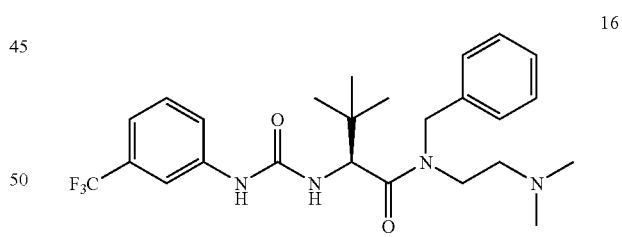

The method of Example 18 was used with N'-benzyl-N,N-dimethylethylenediamine in place of (3S)-(+)-1-benzyl-3-(methylamino)pyrrolidine. Coupling of amine and carboxylic acid: N'-benzyl-N,N-dimethylethylenediamine (2.170 mL, 11.2 mmol), Boc-L-α-tbutylglycine (1.296 g, 5.61 mmol), TFFH (1.482 g, 5.61 mmol), DCM (20 mL). Purification by flash column chromatography using 3% 2M NH₃ in EtOH/DCM provided the desired amide (1.117 g, 51%). This amide could then be deprotected with 40% TFA/DCM as outlined in example 18 to provide the desired amine which was coupled to the requisite isocyanate using the procedure and stoichiometry as in Example 18. 16: LRMS calculated for $C_{25}H_{33}F_3N_4O_2$ 478.26, found 478.04.

EXAMPLE 27

N-Benzyl-N-(2-dimethylamino-ethyl)-3,3-dimethyl-2-[3-(4-trifluoromethoxy-phenyl)-ureido]-butyramide (17)

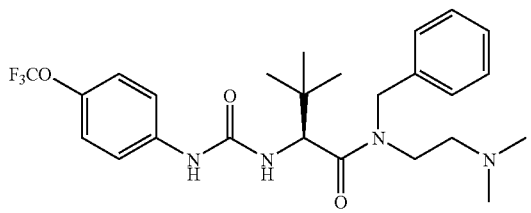

17

The method of Example 18 was used with N'-benzyl-N,N-dimethylethylenediamine in place of (3S)-(+)-1-benzyl-3-(methylamino)pyrrolidine and 4-trifluoromethyoxyphenyl isocyanate in place of α,α,α-trifluoro-m-tolyl isocyanate. Coupling of amine and carboxylic acid: N'-benzyl-N,N-dimethylethylenediamine (2.170 mL, 11.2 mmol), Boc-L-α-tbutylglycine (1.296 g, 5.61 mmol), TFFH (1.482 g, 5.61 mmol), DCM (20 mL). Purification by flash column chromatography using 3% 2M $NH_3$ in EtOH/DCM provided the desired amide (1.117 g, 51%). This amide could then be deprotected with 40% TFA/DCM as outlined in Example 18 to provide the desired amine (405 mg, 1.39 mmol) which could be coupled to 4-trifluoromethyoxyphenyl isocyanate (0.210 mL, 1.39 mmol) in DCM (4 mL) using the procedure of Example 18. Purification by flash column chromatography using a gradient of 2 to 5% 2M $NH_3$ in EtOH/DCM provided the desired 17 (137 mg, 20%). 17: LRMS calculated for $C_{25}H_{33}F_3N_4O_3$ 494.25, found 495.05.

EXAMPLE 28

N-(1-Benzyl-2-dimethylamino-ethyl)-3,3-dimethyl-2-[3-(3-trifluoromethyl-phenyl)-ureido]-butyramide (18)

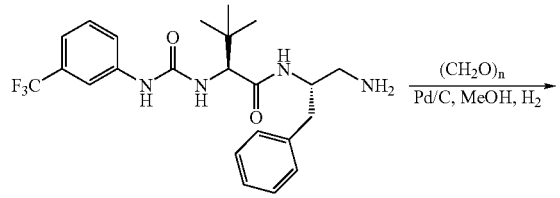

4

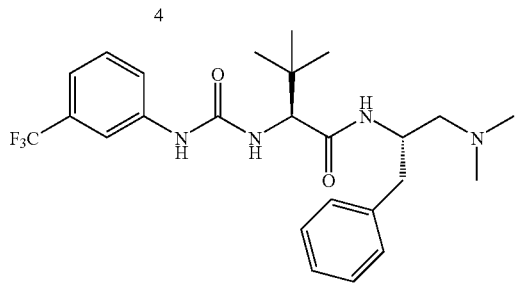

18

A solution of 4 (120 mg, 0.267 mmol) in MeOH (2 mL) was purged with Ar before adding Pd/C (approx. 15 mg) followed by paraformaldehyde (32 mg, 1.1 mmol). The mixture was allowed to stir under an atmosphere of hydrogen at room temperature overnight. The reaction mixture was then filtered through a plug of celite, washing with MeOH, and concentrated in vacuo. The residue was purified via preparative thin layer chromatography using 1% MeOH/EtOAc to provide 18. 18: LRMS calculated for $C_{25}H_{33}F_3N_4O_2$ 478.26, found 477.87.

EXAMPLE 29

N-(1-Benzyl-pyrrolidin-3-yl)-3,3-dimethyl-2-[3-(4-trifluoromethoxy-phenyl)-ureido]-butyramide (19)

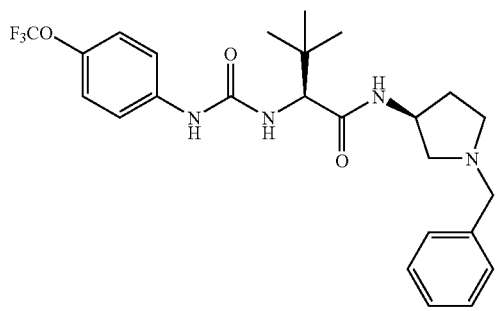

19

The method of Example 10 was used with 4-trifluoromethoxyphenyl isocyanate instead of α,α,α-trifluoro-m-tolyl isocyanate: 2b (137 mg, 0.474 mmol), 4-trifluoromethoxyphenyl isocyanate (0.079 mL, 0.569 mmol), DCM (1 mL). Purification by flash column chromatography using a gradient of 2 to 5% 2M $NH_3$ in EtOH/DCM provided the desired 19 (173 mg, 74%). LRMS calculated for $C_{25}H_{31}F_3N_4O_3$ 492.23, found 492.81.

EXAMPLE 30

Combinatorial Preparation of Urea Analogues (See also FIGS. 1-6)

The method outlined in Example 17 above (with the exception of the borane reduction step) was used in a library format.

Abbreviations of the common amino acids are in accordance with the recommendations of IUPAC-IUB. Additional abbreviations include the following: Fmoc-L-HPA: Fmoc-L-Homophenylalanine; Fmoc-L-BIP=Fmoc-L-4,4'-Biphenylalanine; Fmoc-L-2-NAL=Fmoc-L-2-Naphthylalanine; Fmoc-L-tert-LEU=Fmoc-L-α-tert-butyl-GLY. The Fmoc-protected amino acids were obtained from Novabiochem Corp., Synthetech, Inc., and Advanced ChemTech. The corresponding D-enantiomers for the preceding Fmoc-protected amino acids are also included in this disclosure.

Step 1a. Synthesis of Rink resin-bound Fmoc-HPA. N-Fmoc protected Rink Amide resin (4-(2',4'-Dimethoxyphenyl-Fmoc-aminomethyl)-phenoxy resin from Advanced ChemTech, 2×50 g, 0.7 mmole g$^{-1}$) was suspended in a solution (2×500 mL) of 25% piperidine in DMF (v/v) and agitated for 1 hour on an orbital shaker. The solution was removed by filtration, and the resin was washed successively with DMF, MeOH, and DCM (three washes) and then dried in vacuo. Fmoc-L-HPA (21.0 g, 52.5 mmol) was added to a solution of PyBOP® (Benzotriazol-1-yloxy-tris-pyrrolidino-phosphonium hexafluorophosphate, 6 equiv.) in 0.1M NMM (N-Methyl morpholine) in anhydrous DMF (200 mL). This solution was then added to a portion of the dried resin (15.0 g), and the resin slurry was agitated for 3 hours on an orbital shaker. The solution was removed by filtration, and the resin was washed successively with DMF, MeOH, and DCM (three washes) and then dried in vacuo for use in Step 2.

Step 1b. Synthesis of Rink resin-bound Fmoc-BIP. This product can be synthesized according to the procedure described previously in Step 1a, except the Fmoc-L-HPA is replaced with 5 equiv. of Fmoc-L-BIP (24.3 g, 52.5 mmol).

Step 1c. Synthesis of Rink resin-bound Fmoc-2-NAL. This product can be synthesized according to the procedure described previously in Step 1a, except the Fmoc-L-2-NAL is replaced with 5 equiv. of Fmoc-L-2-NAL (22.9 g, 52.5 mmol).

Step 1d. Synthesis of Rink resin-bound Fmoc-PHE. This product can be synthesized according to the procedure described previously in Step 1a, except the Fmoc-L-PHE is replaced with 5 equiv. of Fmoc-L-PHE (20.3 g, 52.5 mmol).

Step 2a. Synthesis of Rink resin-bound Fmoc-tert-LEU-HPA. The Rink resin-bound Fmoc-L-BIP (2.0 g) was suspended in a solution (40 mL) of 25% piperidine in DMF (v/v) and agitated for 1 hour on an orbital shaker. The solution was removed by filtration, and the resin was washed successively with DMF, MeOH, and DCM (three washes) and then dried in vacuo. Fmoc-L-tert-LEU (38.4 mmole, 10 equiv.) was added to a solution of PyBOP® (10 equiv.) in 0.1M NMM in anhydrous DMF (50 mL). This solution was then added to the dried resin (4.8 g), and the resin slurry was agitated for 3 hours on an orbital shaker. The solution was removed by filtration, and the resin was then washed successively with DMF, MeOH, and DCM (three washes) and then dried in vacuo for use in Step 3.

Steps 2b-2d. Synthesis of Rink resin-bound Fmoc-tert-LEU-BIP, Fmoc-tert-LEU-2-NAL, Fmoc-tert-LEU-PHE. The corresponding Rink resin-bound Fmoc-tert-LEU-aal can be synthesized according to the procedure described previously in Step 2a, except the Rink resin-bound Fmoc-BIP can be replaced with the appropriate Rink resin-bound Fmoc-aal (same stoichiometry).

Synthesis of Rink resin-bound Fmoc-PRO-HPA, Fmoc-PRO-BIP, Fmoc-PRO-2-NAL, Fmoc-PRO-PHE. The corresponding Rink resin-bound Fmoc-PRO-aal can be synthesized according to the procedures described previously in Steps 2a-2d, except the Fmoc-tert-LEU is replaced with Fmoc-Pro (same stoichiometry).

Synthesis of Rink resin-bound Fmoc-D-stereoisomers. The corresponding Rink resin-bound Fmoc-D-stereoisomers, enantiomers and diastereomers, can be synthesized according to the procedures described previously in Steps 1 and 2 when the appropriate Fmoc-L-amino acid is replaced with the corresponding Fmoc-D-amino acid.

Each of the 8 resins was evenly distributed in 12 separate wells of a 96-deep well plate.

Step 3. Synthesis of N1-[[(3-Bromophenyl)amino]carbonyl]-tert-LEU-HPA-NH$_2$. The Rink resin-bound Fmoc-tert-LEU-HPA was suspended in a solution (25 mL) of 25% piperidine in DMF (v/v) and agitated for 1 hour on an orbital shaker. The solution was removed by filtration, and the resin was then washed successively with DMF, MeOH, and DCM (three washes) and then dried in vacuo. To a portion of the dried resin (0.100 g) in a 96-deep well plate was added a solution of 3-bromophenyl isocyanate (12.5 equiv.) in anhydrous DMF (0.5 mL). The resin slurry was agitated for 18 hours on an orbital shaker, and then washed successively with DMF, MeOH, and DCM (three times). The Rink resin-bound compound was cleaved from the solid support by agitating the resin with 50% TFA in DCM (v/v) for 30 min followed by filtration and removal of the solvent in vacuo to give N1-[[(3-Bromophenyl)amino]carbonyl]-tert-LEU-BPA-NH$_2$.

The following 12 isocyanates (12.5 equiv.) were each evenly distributed through 8 wells (each containing a different resin) of the 96-deep well plate to give the corresponding product: 3-bromophenyl isocyanate; 4-chlorophenyl isocyanate; 3,4-dichlorophenyl isocyanate; 3-methoxyphenyl isocyanate; 3-(trifluoromethyl)phenyl isocyanate; cyclohexyl isocyanate; 3,5-bis(trifluoromethyl)phenyl isocyanate; 2,6-dimethylphenyl isocyanate; 4-(methylthio)phenyl isocyanate; 4-(trifluoromethoxy)phenyl isocyanate; 2-chloro-5-(trifluoromethyl)phenyl isocyanate; 2,5-difluorophenyl isocyanate.

EXAMPLE 31

Ion Channel and Opiate Receptor Binding of Certain Compounds of the Present Invention (IC$_{50}$s)

The opioid (μ) receptor binding capabilities of compounds described herein were determined according to the procedures outlined by Wang et al. (*FEBS Letters* 1994, 338, 217). The sodium channel receptor binding capabilities of compounds described herein were determined according to the procedures outlined by Catterall et al. (*J. Biol. Chem.* 1981, 256, 8922). The calcium channel receptor binding capabilities of compounds described herein were determined according to the procedures outlined by Gould et al. (*Proc. Natl. Acad. Sci.* USA 1982, 79, 3656), Ehlert et al. (*Life Sci.* 1982, 30, 2191), Reynolds et al. (*J. Pharmacol. Exp. Ther.* 1986, 237, 731), Moresco et al. (*Neurobiology of Aging* 1990, II, 433) and Schoemaker et al. (*Eur. J. Pharmacol.* 1985, III, 273). The potassium channel receptor binding capabilities of compounds described herein were determined according to the procedures outlined by Taylor et al. (*J. Biol. Chem.* 1984, 259, 13957), Rehm et al. (*Proc. Natl. Acad. Sci.* USA 1988, 85, 4919), Vasquez et al. (*J. Biol. Chem.* 1990, 265, 15564) and Mourre et al. (*Brain Research* 1986, 382, 239).

| Compound | μ (μM) | Na (site 2) (μM) | Ca (type L, B*) (μM) | Ca (type L, D*) (μM) | Ca (type L, P*) (μM) | Ca (type N) (μM) | K** (μM) |
|---|---|---|---|---|---|---|---|
| 3a | >1 | <1 | NT | NT | >1 | >1 | >1 |
| 3b | <1 | <0.1 | NT | NT | >1 | >1 | >1 |
| 3c | >1 | <1 | NT | NT | >1 | >1 | >1 |
| 3d | >1 | <1 | NT | NT | >1 | >1 | >1 |
| 3e | >1 | <0.1 | >1 | >1 | <1 | >1 | >1 |
| 3f | >1 | <0.1 | >1 | >1 | <1 | >1 | >1 |
| 3g | >1 | <0.1 | >1 | >1 | <1 | >1 | >1 |
| 3h | >1 | <0.1 | >1 | >1 | <1 | >1 | >1 |
| 4 | <0.1 | <0.1 | <1 | >1 | <1 | >1 | >1 |
| 5 | >1 | <0.1 | <1 | >1 | <1 | >1 | >1 |
| 8 | >1 | <0.1 | <1 | >1 | <1 | >1 | >1 |

| Compound | μ (μM) | Na (site 2) (μM) | Ca (type L, B*) (μM) | Ca (type L, D*) (μM) | Ca (type L, P*) (μM) | Ca (type N) (μM) | K** (μM) |
| --- | --- | --- | --- | --- | --- | --- | --- |
| 9 | >1 | <0.1 | >1 | >1 | <1 | >1 | >1 |
| 10 | >1 | <1 | <1 | <0.1 | <1 | >1 | >1 |
| 11 | >1 | <0.1 | <1 | >1 | <1 | >1 | >1 |
| 15 | >1 | >1 | NT | NT | >1 | >1 | NT |
| 16 | >1 | <1 | >1 | >1 | >1 | >1 | NT |
| 17 | >1 | <0.1 | >1 | >1 | <1 | >1 | NT |
| 18 | <0.1 | <1 | >1 | >1 | >1 | >1 | >1 |
| 19 | >1 | <1 | >1 | <1 | <1 | >1 | NT |
| 22 | NT | <1 | >1 | >1 | >1 | >1 | NT |

*Calcium type L: B = benzothiazepine site; D = dihydropyridine site; P = phenylalkylamine site.
**Potassium refers to potassium channel $[K_A]$, $[K_V]$ or $[SK_{Ca}]$.
NT = Not tested

EXAMPLE 32
Pyrrolidine-1,2-dicarboxylic acid 2-[benzyl-(2-dimethylamino-ethyl)-amide] 1-[(4-trifluoromethoxy-phenyl)-amide] (22)

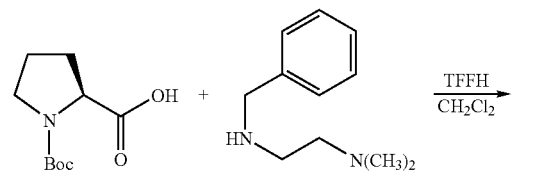

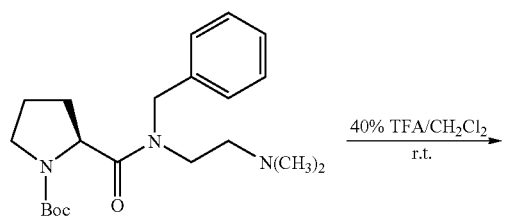

20

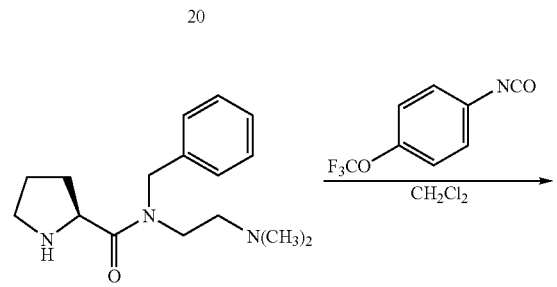

21

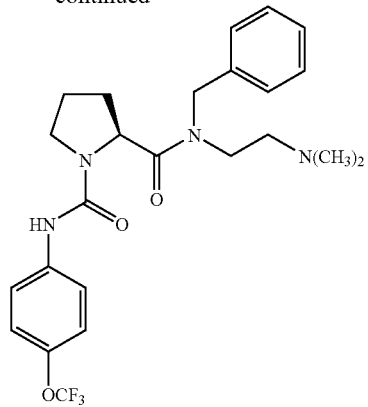

22

To a solution of N-Boc-L-proline (2.0 g, 9.3 mmol) in dichloromethane (20 mL) was added TFFH (2.45 g, 9.3 mmol). The mixture was cooled to 0° C. and N'-benzyl-N,N-dimethylethylenediamine (3.31 g, 18.6 mmol) was added to the reaction. The reaction was allowed to warm to room temperature and stirred for 6 h. The reaction was then quenched with water (20 mL), and the organic layer was dried over anhydrous sodium sulfate, filtered and concentrated. The organic residue was purified by flash chromatographey on silica gel, eluting with dichloromethane/2.0 M ammonia in ethyl alcohol (96:4) to give 20 (1.21 g, 35%) as a pale yellow oil.

A solution of 20 (1.1 g, 2.93 mmol) in 40% trifluoroacetic acid/dichloromethane (20 mL) was stirred at room temperature for 4 h. The solvent was removed by rotary evaporation, and the resulting organic residue was carefully partitioned between dichloromethane and a saturated solution of sodium bicarbonate (40 mL each). The organic extract was dried over anhydrous sodium sufate, filtered, and concentrated to give 21 (0.75 g, 93%) as a light brown oil. This amine was used in the next step without further purification.

4-(Trifluoromethoxy)phenyl isocyanate (0.15 g, 0.74 mmol) was slowly added to a solution of 21 (0.20 g, 0.73 mmol) in dichloromethane (25 mL) at 0° C. The solution was allowed to warm to room temperature and stirred for 18 h. The reaction was then quenched with water (20 mL), and the organic layer was dried over anhydrous sodium sulfate, filtered and concentrated. The organic residue was purified by flash chromatographey on silica gel, eluting with dichloromethane/2.0 M ammonia in ethyl alcohol (96:4) to give 22 (0.17 g, 49%) as a white solid; $C_{24}H_{29}F_3N_4O_3$: LRMS=479 (MH+).

EXAMPLE 33
Opiate Tissue Binding of a Compound of the Present Invention ($EC_{50}$s)

The opioid (μ) agonist or antagonist capabilities of compounds described herein were determined in guinea pig ileum according to the procedures outlined by Maguire P et al. See Eur. J. Pharmacol. 1992, 213, 219.

| Compound | μ agonist ($EC_{50}$, μM) | μ antagonist ($EC_{50}$, μM) |
| --- | --- | --- |
| 4 | 0.250 | |

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by general structure A:

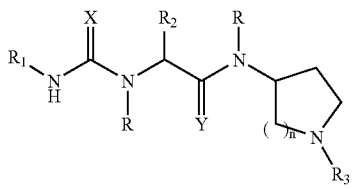

A wherein
- X represents O or S;
- Y represents $H_2$, O or S;
- R represents independently for each occurrence H, alkyl, aryl, heteroaryl, aralkyl or heteroaralkyl;
- $R_1$ represents alkyl, aryl, heteroaryl, aralkyl or heteroaralkyl;
- $R_2$ represents alkyl, aryl, heteroaryl, aralkyl or heteroaralkyl;
- $R_3$ represents H, alkyl, aryl, heteroaryl, aralkyl, heteroaralkyl or acyl;
- n is 1 or 2; and
- the stereochemical configuration at any stereocenter of a compound represented by A may be R, S, or a mixture of these configurations.

2. A compound represented by general structure C:

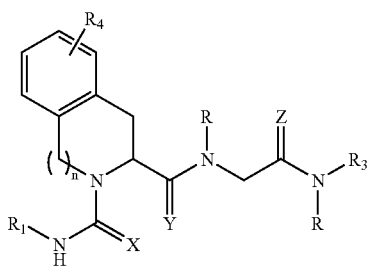

C wherein
- X represents O or S;
- Y represents $H_2$, O or S;
- Z represents $H_2$, O or S;
- R represents independently for each occurrence H, alkyl, aryl, heteroaryl, aralkyl or heteroaralkyl;
- $R_1$ represents alkyl, aryl, heteroaryl, aralkyl or heteroaralkyl;
- $R_3$ represents H, alkyl, aryl, heteroaryl, aralkyl, heteroaralkyl or acyl;
- $R_4$ is absent or present 1, 2, 3 or 4 times;
- $R_4$ represents independently for each occurrence alkyl, aryl, alkenyl, alkynyl, heteroaryl, aralkyl, heteroaralkyl, halogen, —$N(R)_2$, formyl, acyl, —$CO_2R$, —$CONR_2$, —$O_2CR$, acylamino, —SR, or —OR;
- n is 1 or 2; and
- the stereochemical configuration at any stereocenter of a compound represented by C may be R, S, or a mixture of these configurations.

3. The compound represented by general structure D:

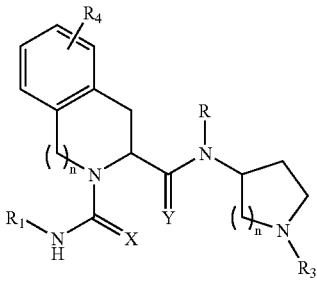

D wherein
- X represents O or S;
- Y represents $H_2$, O or S;
- R represents independently for each occurrence H, alkyl, aryl, heteroaryl, aralkyl or heteroaralkyl;
- $R_1$ represents alkyl, aryl, heteroaryl, aralkyl or heteroaralkyl;
- $R_3$ represents H, alkyl, aryl, heteroaryl, aralkyl, heteroaralkyl or acyl;
- $R_4$ is absent or present 1, 2, 3 or 4 times;
- $R_4$ represents independently for each occurrence alkyl, aryl, alkenyl, alkynyl, heteroaryl, aralkyl, heteroaralkyl, halogen, —$N(R)_2$, formyl, acyl, —$CO_2R$, —$CONR_2$, —$O_2CR$, acylamino, —SR, or —OR;
- n is independently for each occurrence 1 or 2; and
- the stereochemical configuration at any stereocenter of a compound represented by D may be R, S, or a mixture of these configurations.

4. A formulation, comprising a compound of claim 1, 2, or 3; and a pharmaceutically acceptable excipient.

5. A method of treating pain, drug addiction, or tinnitus in a mammal, comprising the step of administering to a mammal in need thereof a therapeutically effective amount of a compound of claim 1, 2, or 3.

* * * * *